(12) United States Patent
Butler et al.

(10) Patent No.: US 10,932,827 B2
(45) Date of Patent: Mar. 2, 2021

(54) SYSTEMS AND METHODS FOR SPINAL ROD INSERTION AND REDUCTION

(71) Applicant: Life Spine, Inc., Huntley, IL (US)

(72) Inventors: Michael S. Butler, St. Charles, IL (US); Danish Siddiqui, Northbrook, IL (US); Daniel Predick, West Lafayette, IN (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 15/948,644

(22) Filed: Apr. 9, 2018

(65) Prior Publication Data

US 2018/0235676 A1    Aug. 23, 2018

Related U.S. Application Data

(63) Continuation of application No. 15/468,756, filed on Mar. 24, 2017, now Pat. No. 9,936,986, which is a continuation of application No. 14/821,015, filed on Aug. 7, 2015, now Pat. No. 9,603,628, which is a
(Continued)

(51) Int. Cl.
| | | |
|---|---|---|
| *A61B 17/70* | (2006.01) | |
| *A61B 17/86* | (2006.01) | |
| *A61B 17/88* | (2006.01) | |
| *A61B 90/00* | (2016.01) | |

(52) U.S. Cl.
CPC ...... *A61B 17/7086* (2013.01); *A61B 17/7002* (2013.01); *A61B 17/7032* (2013.01); *A61B 17/7074* (2013.01); *A61B 17/7076* (2013.01); *A61B 17/7082* (2013.01); *A61B 17/7083* (2013.01); *A61B 17/7085* (2013.01); *A61B 17/7091* (2013.01); *A61B 17/8605* (2013.01);
(Continued)

(58) Field of Classification Search
CPC ............ A61B 17/7091; A61B 17/7086; A61B 17/7082; A61B 17/7074; A61B 17/7076; A61B 17/7032; A61B 17/7085; A61B 17/7083
USPC ....................................................... 606/86 A
See application file for complete search history.

(56) References Cited

U.S. PATENT DOCUMENTS

| | | | |
|---|---|---|---|
| 2,062,882 A | 12/1936 | Heinrich | |
| 2,102,896 A | 12/1937 | Heinrich | |
| 5,429,532 A | 7/1995 | Auclair | |

(Continued)

FOREIGN PATENT DOCUMENTS

| | | |
|---|---|---|
| DE | 44 36 262 | 7/1996 |
| DE | 19829699 | 1/2000 |

OTHER PUBLICATIONS

European Search Report for European Application No. 14167071.1, dated Nov. 6, 2014, 18 pages.
(Continued)

*Primary Examiner* — Nicholas J Plionis
(74) *Attorney, Agent, or Firm* — Foley & Lardner LLP

(57) ABSTRACT

A guide assembly includes a spinal screw assembly having a bone screw and a spinal rod holder; and a spinal rod guide having first and second elongated arc portions defining a pair of longitudinal slots extending along the first and second arc portions, each of the first and second arc portions further defining at least one recess extending transversely from each of the longitudinal slots, the at least one recess configured to receive at least a portion of a reduction tool to enable reduction of a spinal rod received within the spinal rod holder.

19 Claims, 14 Drawing Sheets

Related U.S. Application Data continuation of application No. 13/888,269, filed on May 6, 2013, now Pat. No. 9,125,694.

(52) U.S. Cl.
CPC ...... *A61B 17/8863* (2013.01); *A61B 17/7037* (2013.01); *A61B 2090/037* (2016.02)

(56) References Cited

U.S. PATENT DOCUMENTS

| | | | |
|---|---|---|---|
| 5,681,319 A | 10/1997 | Biedermann et al. | |
| 5,823,804 A | 10/1998 | Auclair | |
| 5,872,833 A | 2/1999 | Scherer | |
| 5,873,878 A | 2/1999 | Harms et al. | |
| 5,882,350 A | 3/1999 | Ralph et al. | |
| 6,010,503 A | 1/2000 | Richelsoph et al. | |
| 6,074,391 A | 6/2000 | Metz-Stavenhagen et al. | |
| 6,248,104 B1 | 6/2001 | Chopin et al. | |
| 6,648,888 B1 | 11/2003 | Shluzas | |
| 6,740,086 B2 | 5/2004 | Richelsoph | |
| 6,743,231 B1 | 6/2004 | Gray et al. | |
| 7,261,714 B2 | 8/2007 | Richelsoph | |
| 7,955,363 B2 | 6/2011 | Richelsoph | |
| 8,388,659 B1 | 3/2013 | Lab et al. | |
| 8,409,255 B2 | 4/2013 | Richelsoph | |
| 9,066,761 B2* | 6/2015 | McBride | A61B 17/708 |
| 10,136,927 B1* | 11/2018 | Lish | A61B 17/7086 |
| 2003/0130659 A1 | 7/2003 | Haider | |
| 2006/0025771 A1 | 2/2006 | Jackson | |
| 2006/0111715 A1* | 5/2006 | Jackson | A61B 17/861 |
| | | | 128/897 |
| 2006/0184178 A1* | 8/2006 | Jackson | A61B 17/7011 |
| | | | 606/99 |
| 2006/0271050 A1 | 11/2006 | Piza Vallespir | |
| 2006/0276792 A1 | 12/2006 | Ensign et al. | |
| 2007/0078460 A1 | 4/2007 | Frigg et al. | |
| 2007/0167951 A1* | 7/2007 | Ainsworth | A61B 17/025 |
| | | | 606/90 |
| 2007/0191840 A1 | 8/2007 | Pond et al. | |
| 2007/0270867 A1 | 11/2007 | Miller et al. | |
| 2008/0082103 A1 | 4/2008 | Hutton et al. | |
| 2008/0119849 A1* | 5/2008 | Beardsley | A61B 17/7032 |
| | | | 606/306 |
| 2008/0228228 A1 | 9/2008 | Hestad et al. | |
| 2008/0243190 A1* | 10/2008 | Dziedzic | A61B 17/7091 |
| | | | 606/278 |
| 2010/0036443 A1* | 2/2010 | Hutton | A61B 17/7032 |
| | | | 606/86 R |
| 2010/0228090 A1 | 9/2010 | Weisenburgh et al. | |
| 2010/0292742 A1* | 11/2010 | Stad | A61B 17/7091 |
| | | | 606/86 A |
| 2011/0040328 A1* | 2/2011 | Miller | A61B 17/7091 |
| | | | 606/246 |
| 2011/0178560 A1 | 7/2011 | Butler et al. | |
| 2011/0257692 A1* | 10/2011 | Sandstrom | A61B 17/7085 |
| | | | 606/86 A |
| 2012/0031792 A1 | 2/2012 | Petit | |
| 2012/0109208 A1 | 5/2012 | Justis et al. | |
| 2012/0259338 A1 | 10/2012 | Carr et al. | |
| 2013/0018419 A1* | 1/2013 | Rezach | A61B 17/7076 |
| | | | 606/264 |

OTHER PUBLICATIONS

Partial European Search Report for Application No. 14167071.1, dated Aug. 22, 2014, 7 pages.

\* cited by examiner

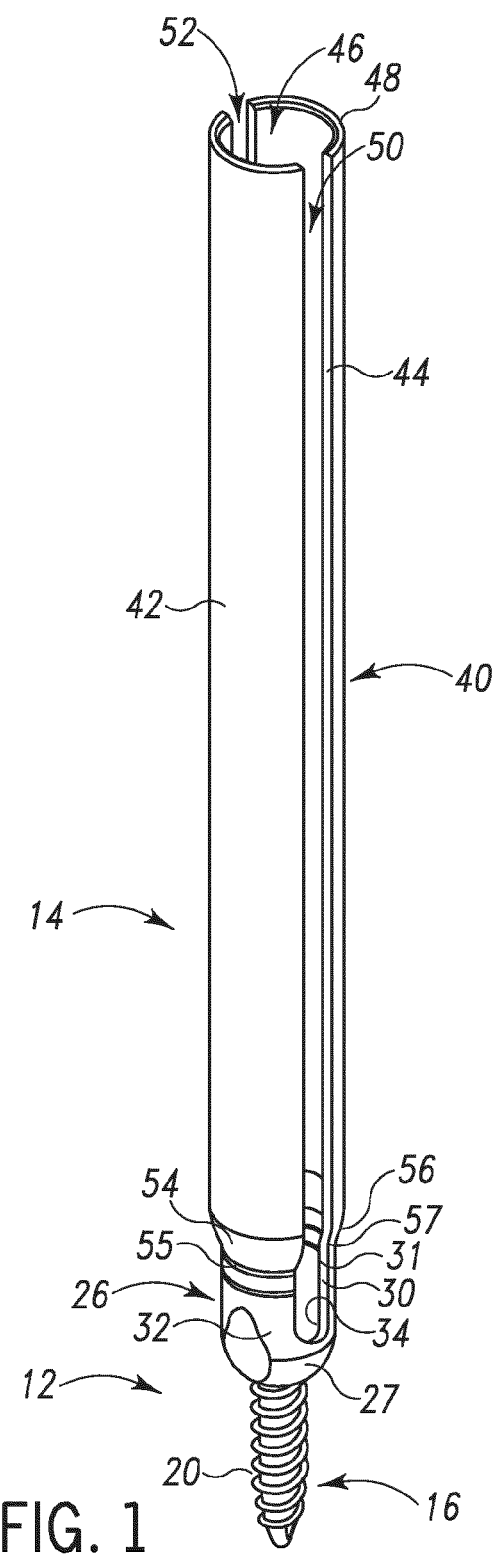
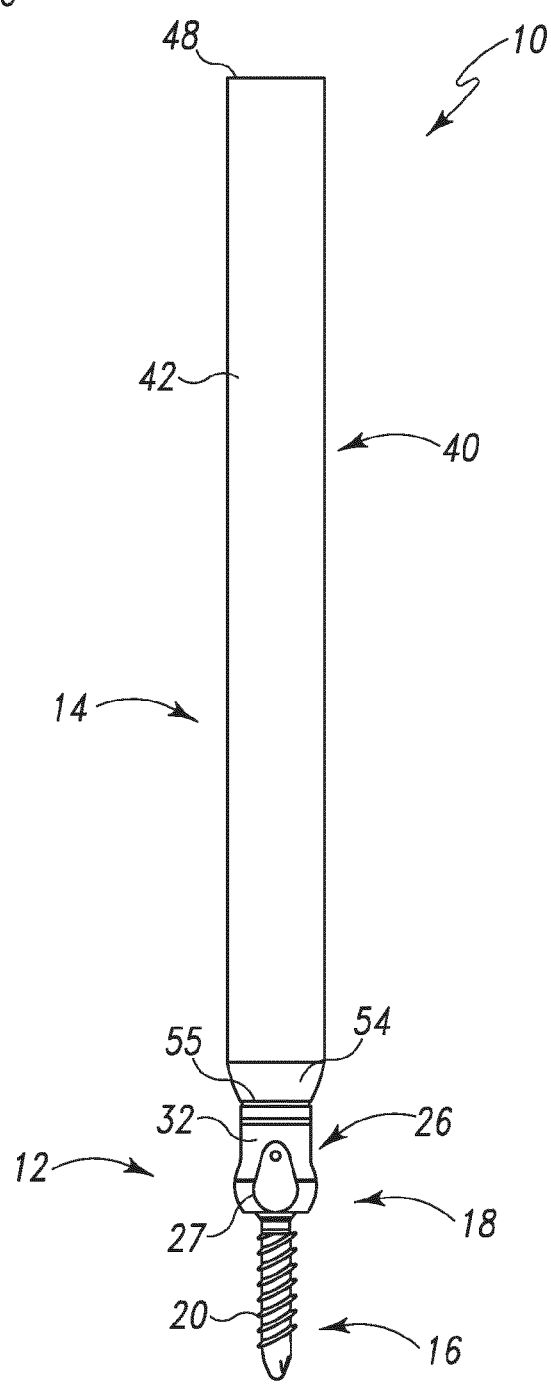
FIG. 1
FIG. 2

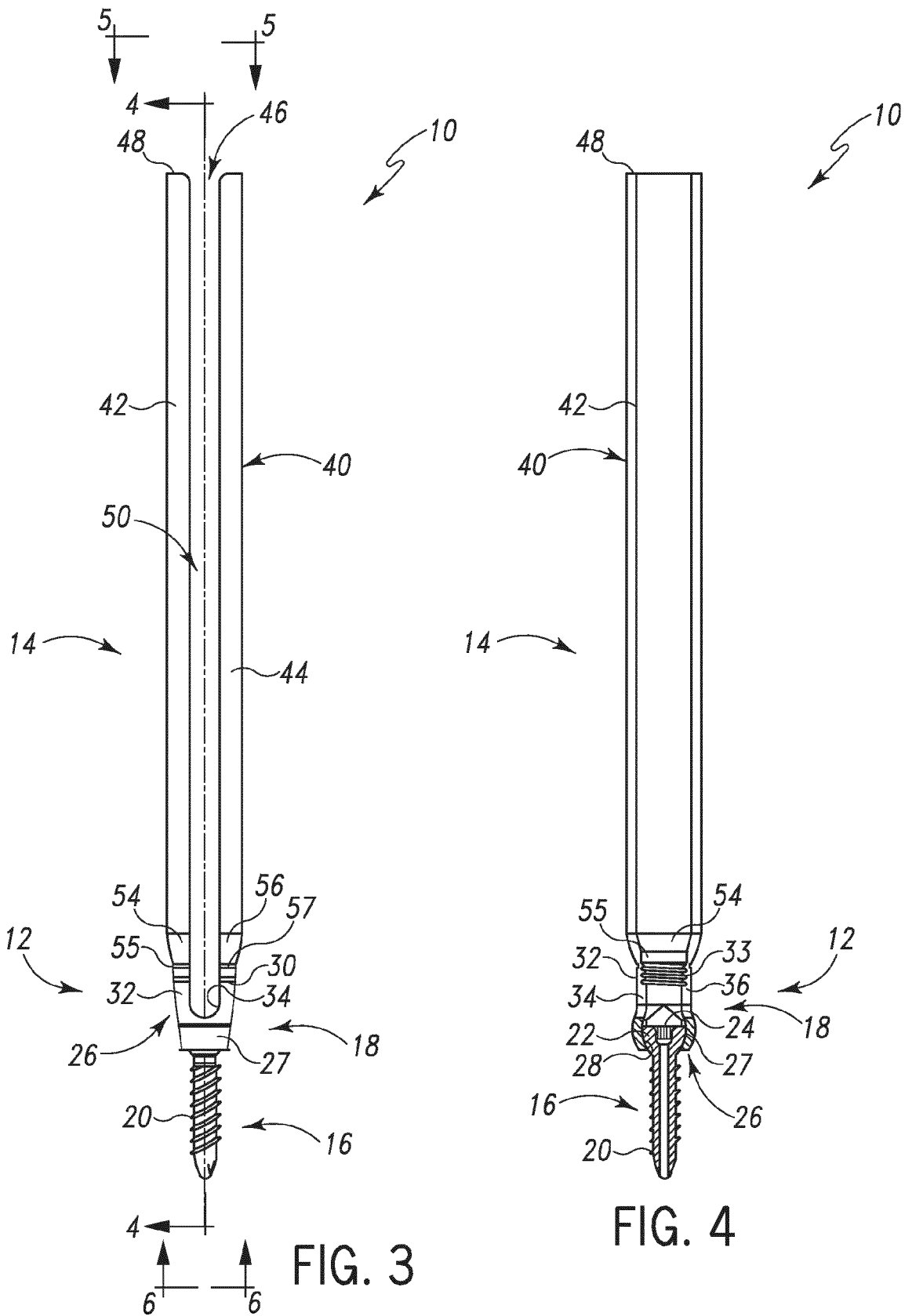

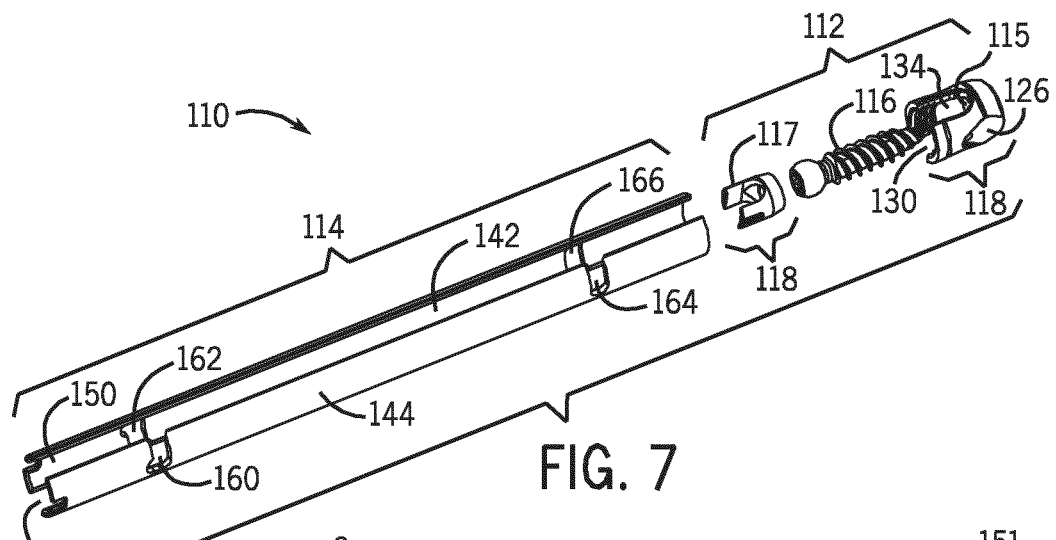
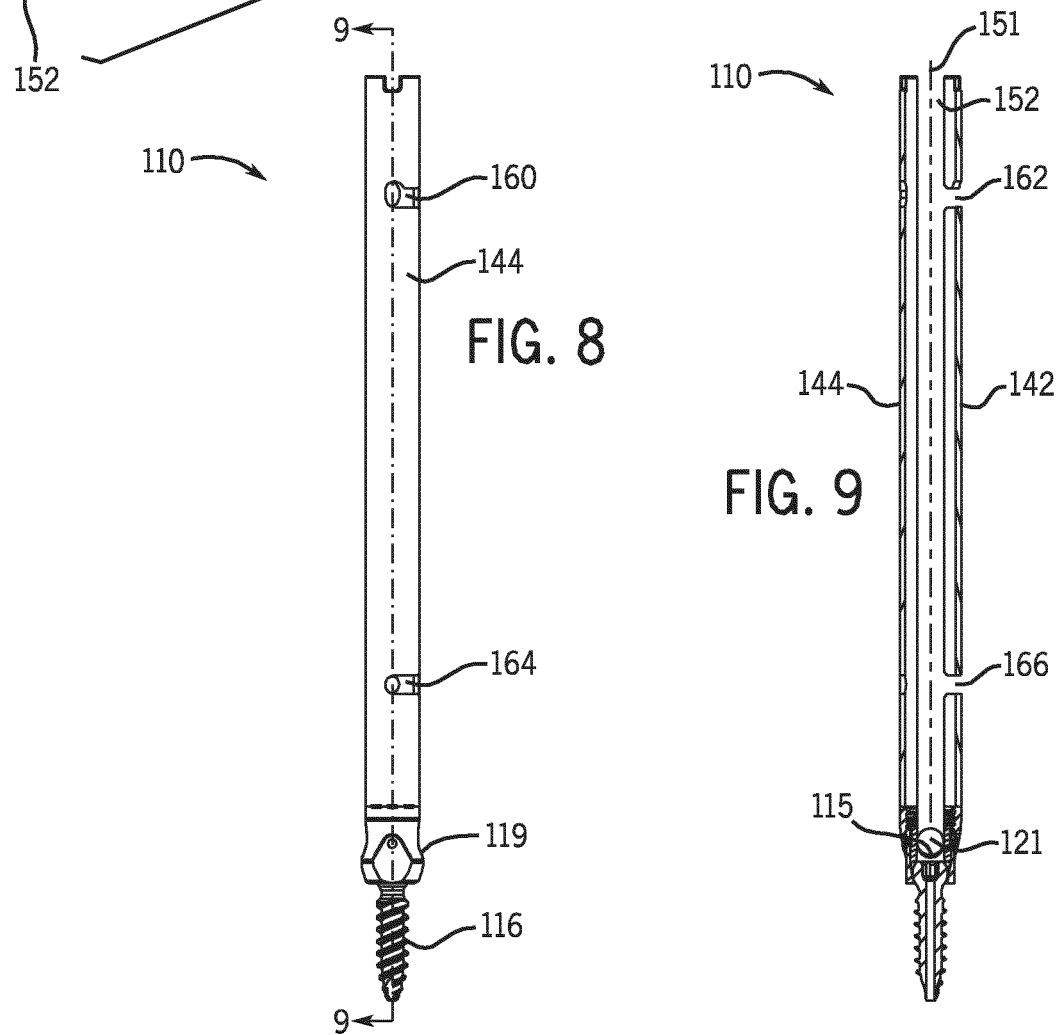

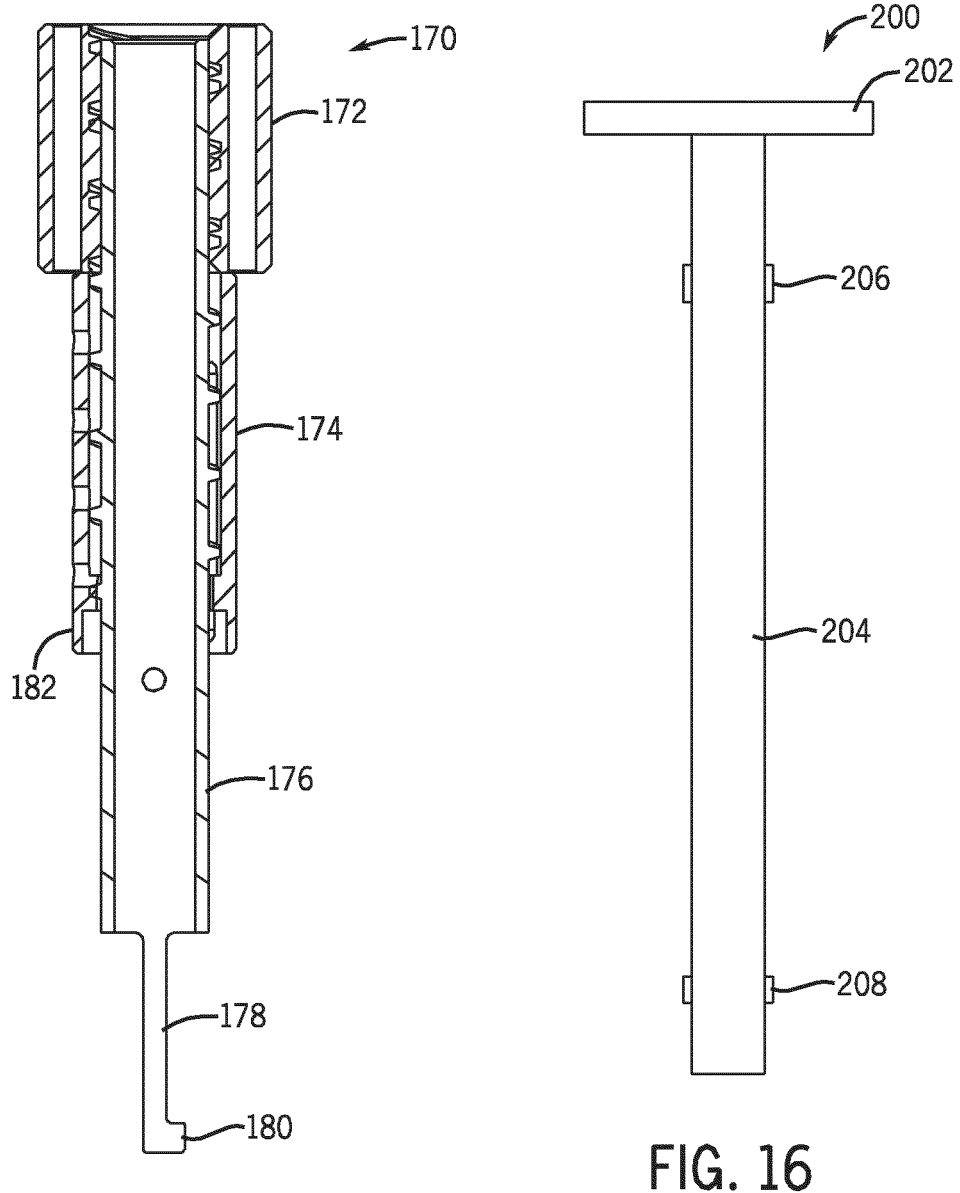

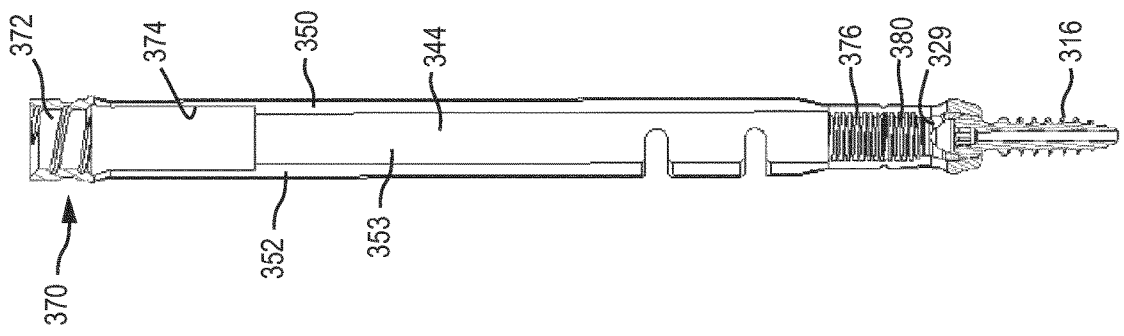
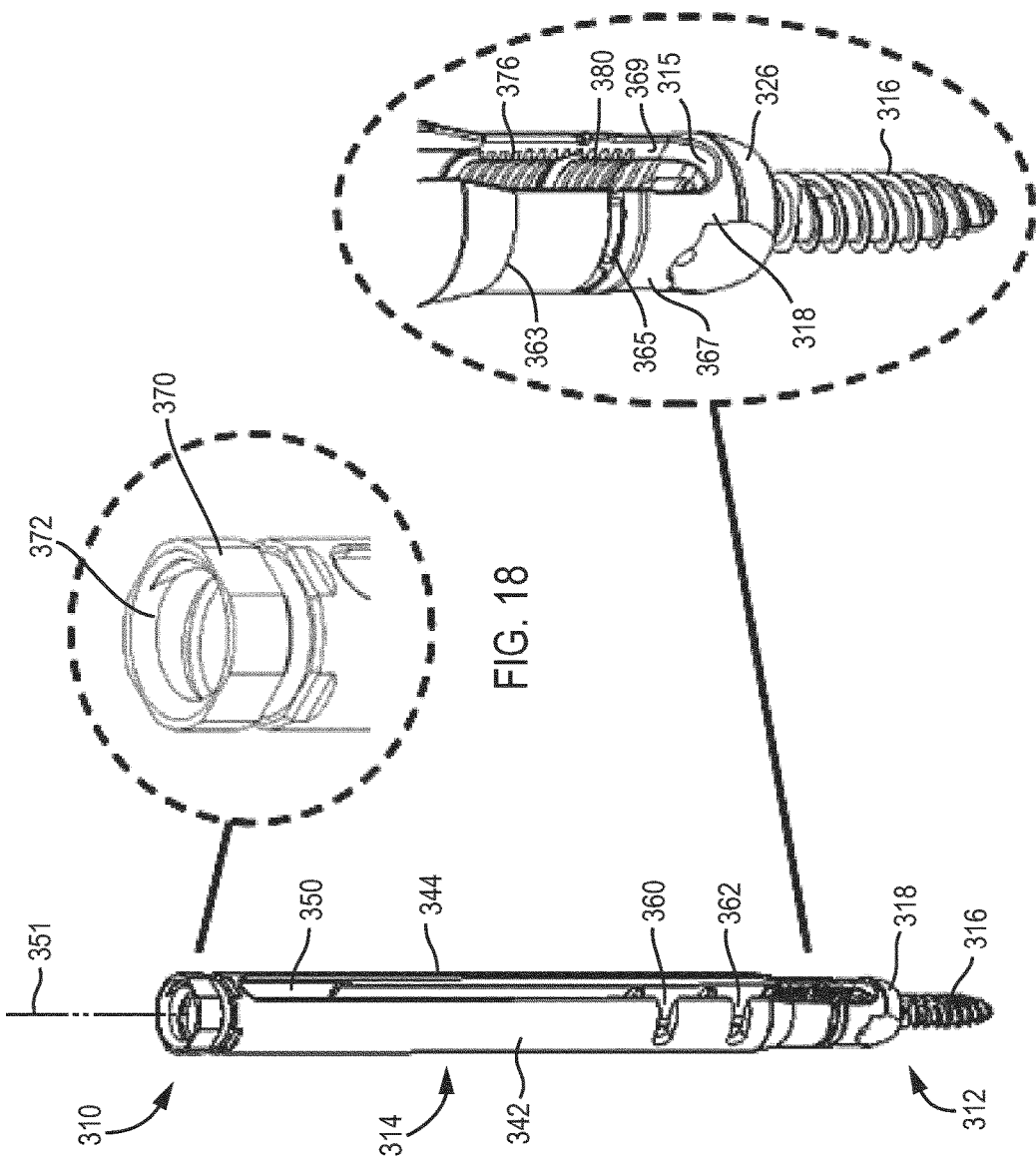
FIG. 20
FIG. 19
FIG. 18
FIG. 17

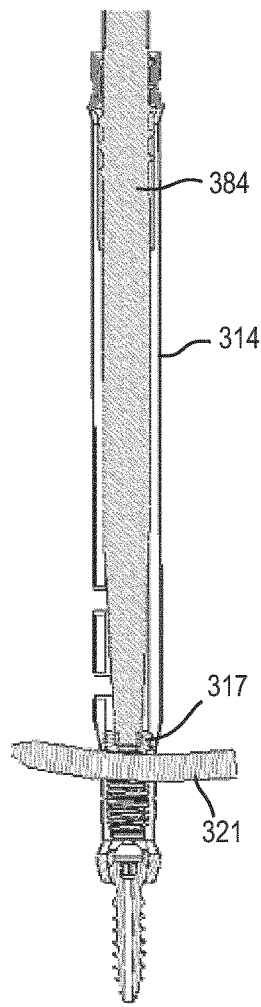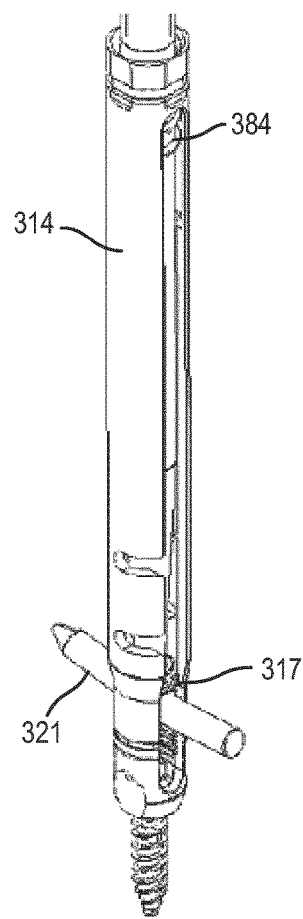
FIG. 26          FIG. 25
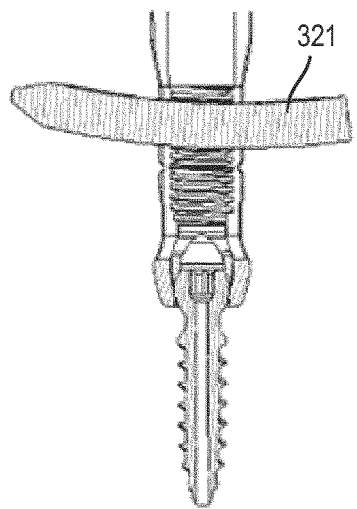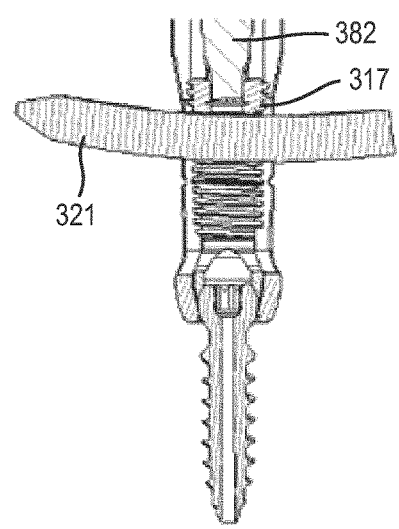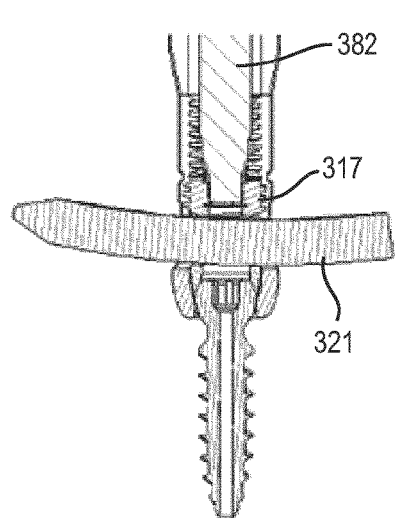
FIG. 27          FIG. 28          FIG. 29

SYSTEMS AND METHODS FOR SPINAL ROD INSERTION AND REDUCTION

CROSS-REFERENCE TO RELATED PATENT APPLICATIONS

This application is a continuation of U.S. patent application Ser. No. 15/468,756, filed Mar. 24, 2017, which is a continuation of U.S. patent application Ser. No. 14/821,015, filed Aug. 7, 2015, which is a continuation of U.S. patent application Ser. No. 13/888,269, filed May 6, 2013, both of which are incorporated herein by reference in their entireties.

BACKGROUND

The present disclosure relates to spine fixation components, constructs and assemblies and, more particularly, to a construct for the implantation of a spinal rod.

Spinal orthopedic assemblies and constructs such as spine plates, spinal bone screw assemblies for spinal rods and other devices (spinal components) have made a profound contribution to the correction of spinal deformities, accidents and other problems in the thoracic, lumbar and sacral spine. These and other spinal devices are fixed to vertebrae using vertebral bone screws. Vertebral bone screws are specially designed and manufactured bone screws that are placed into the bone of a vertebra. One typical placement of a bone screw for the fixation of a spinal component is through a pedicle of the vertebral body. Vertebral bone screws placed in this manner offer superior strength and pull-out resistance as compared to other forms of fixation in spine surgery. The ability to achieve pedicle fixation has allowed surgeons to obtain more secure fixation of the involved vertebral segments, which permits more powerful correction of spine problems and reported better clinical outcomes. Vertebral bone screws for pedicle fixation are typically known as pedicle screws.

Of the various spinal components, spinal rods are used in certain circumstances to fix a number of vertebrae in a particular orientation. As such, spinal rods must be fixed to the vertebrae. The pedicle screw provides a solid foundation for the attachment of a spinal rod. In one form, a spinal rod may be held relative to a pedicle screw by a spinal rod connector that is coupled to the pedicle screw. The spinal rod connector is typically rotationally connected to the pedicle screw in order to allow various connection orientations of the spinal rod relative to the longitudinal axis of the pedicle screw. The spinal rod connector includes features that allow the reception and capture of the spinal rod. This is accomplished by placing the spinal rod through an opening in the body via which the pedicle screw and spinal rod connector is attached to the vertebra. The spinal rod is then placed through the body opening and directed into and oriented on the spinal rod connector. Thereafter, the spinal rod must be secured to each individual spinal rod connector. This is typically accomplished by installing a spinal rod connector screw onto the spinal rod connector via a tube temporarily connected to the spinal rod connector. Because of this complicated procedure, it is fairly difficult and/or cumbersome to situate and mount a spinal rod onto a spinal rod connector of a vertebral bone screw.

In view of the above, it is clear that there is a need for a better manner of mounting a spinal rod onto a spinal rod connector of a vertebral bone screw.

SUMMARY

The present disclosure relates to a spinal rod guide for mounting a spinal rod onto a spinal rod holder of a vertebral bone screw, particularly, but not necessarily, for use in minimally invasive surgery. The spinal rod guide is configured to extend between an opening in a patient's body and the spinal rod holder of the vertebral bone screw, to receive a spinal rod therein, and thereafter accurately guide the spinal rod into the spinal rod holder. The spinal rod guide is defined by a first elongated arc portion and a second elongated arc portion that together define a first elongated slot and a second elongated slot sized for the introduction and placement of the spinal rod into the spinal rod holder.

The first and second elongated arc portions together define an elongated tube that allows additional spinal rod components to be guided and placed into/onto the spinal rod connector, particularly, but not necessarily, for securing the spinal rod into the spinal rod holder.

An embodiment of the spinal rod guide comprises a first elongated arc portion that is attachable to a spine rod holder of a spinal rod bone screw assembly and a second elongated arc portion that is attachable to the spine rod holder of the spinal rod bone screw assembly. First and second longitudinal slots are defined between sides of the first and second arc portions and which extend from a top of the elongated arc portions to a bottom of the elongated arc portions. The two longitudinal slots are situated at diametrically opposite sides thereof. Each longitudinal slot aligns with a spinal rod slot of the spinal rod holder to thereby allow easy placement of the spinal rod into the spinal rod holder. Thereafter, the elongated arc portions provide direct communication and alignment with the top of the spinal rod holder by defining an elongated tube in order to receive a spinal rod holder drive screw for securing the spinal rod into the spinal rod holder. In this embodiment, the spinal rod guide is removed from the spinal rod holder after installation and securing of the spinal rod.

The present disclosure also relates to a spinal rod guide assembly for mounting a spinal rod into a spinal rod holder of a vertebral bone screw assembly of the spinal rod guide assembly particularly, but not necessarily, for use in minimally invasive surgery. The spinal rod guide assembly includes a spinal rod guide that is initially attached to the spinal rod holder of the vertebral bone screw assembly. The spinal rod guide is configured to extend from an opening in a patient's body to the spinal rod connector, to receive a spinal rod therein, and thereafter accurately guide the spinal rod into the spinal rod connector. The spinal rod guide defines a guide tube for the introduction and placement of additional spinal rod components onto the spinal rod connector, particularly, but not necessarily, for securing the spinal rod into the spinal rod holder. The spinal rod guide is temporarily attached to the spinal rod connector in a manner that allows for easy detachment of the spinal rod guide from the spinal rod holder.

An embodiment of the spinal rod guide assembly includes a vertebral bone screw, a spinal rod holder pivotally coupled to the vertebral bone screw, and an elongated guide tube defined by first and second elongated arc portions that are attached onto a top of the spinal rod holder. The elongated guide tube has first and second longitudinal slots extending from a top of the elongated guide tube to a bottom of the elongated guide tube that align with first and second spinal rod slots of the spinal rod holder. The two longitudinal slots of the elongated guide tube and the two spinal slots of the spinal rod holder are situated at diametrically opposite sides. The slots allow easy placement of the spinal rod into the spinal rod holder. The elongated tube moreover provides direct communication and alignment with the top of the spinal rod holder in order to receive a spinal rod connector drive screw for securing the spinal rod into the spinal rod holder. The spinal rod guide is scored or otherwise connected at a junction between the spinal rod guide and the spinal rod holder such that the spinal rod guide is easily broken or snapped off from the spinal rod holder once installation of the spinal rod is complete.

Another embodiment relates to a guide assembly comprising a spinal screw assembly comprising a bone screw and a spinal rod holder; and a spinal rod guide comprising first and second elongated arc portions defining a pair of longitudinal slots extending along the first and second arc portions, each of the first and second arc portions further defining at least one recess extending transversely from each of the longitudinal slots, the at least one recess configured to receive at least a portion of a reduction tool to enable reduction of a spinal rod received within the spinal rod holder.

Another embodiment relates to a spinal rod installation kit comprising a guide assembly comprising a bone screw assembly and a pair of arcuate flanges extending from the screw assembly, the arcuate flanges defining at least one longitudinal slot therebetween; a spinal rod configured to be guided toward a fully seated position by the arcuate flanges; a spacer having a first end and a second end, the second end configured to engage the spinal rod; and a reducer configured to engage the first end of the spacer and having an inner member moveably coupled to an outer member; wherein rotation of the outer member relative to the inner member causes a longitudinal movement of the screw assembly relative to the spinal rod.

Another embodiment relates to a method of reducing a spinal rod, the method comprising securing a spinal rod guide assembly to a vertebral body, the spinal rod guide assembly comprising a spinal screw assembly and a pair of tabs extending therefrom; positioning a spinal rod between the pair of tabs; positioning a spacer having first and second ends over the spinal rod guide assembly such that the second end of the spacer engages the spinal rod; positioning a reducer such that an outer member of the reducer engages the first end of the spacer and an inner member of the reducer engages at least one of the pair of tabs; moving the inner member relative to the outer member to cause a corresponding movement of the spinal screw assembly relative to the spinal rod.

Another embodiment relates to a method of installing a spinal rod, the method comprising providing a spinal rod guide assembly having a spinal screw and a spinal rod holder, wherein a pair of flanges extends from the spinal rod holder; securing the spinal screw to a vertebral body; guiding a spinal rod between the pair of flanges to a desired position relative to the spinal rod holder; applying a torque to the pair of flanges about a longitudinal axis defined by the pair of flanges to break the pair of flanges away from the spinal rod holder; and moving the pair of flanges away from the spinal rod holder.

Another embodiment relates to a guide assembly comprising a spinal screw assembly comprising a bone screw and a spinal rod holder, the spinal rod holder having a threaded portion; a fastener, the fastener configured to be threadingly received by the threaded portion of the spinal rod holder and to engage a surface of a spinal rod; and a spinal rod guide comprising upper and lower spaced apart threaded portions, the upper threaded portion configured to threadingly receive a threaded portion of a reduction tool, the lower threaded portion configured to threadingly receive the fastener; wherein the spinal rod holder is detachably coupled to the spinal rod guide such that the threaded portion of the spinal rod holder and the lower threaded portion of the spinal rod guide enable a user to thread the fastener along both the threaded portion of the spinal rod holder and the lower threaded portion of the spinal rod guide in a continuous manner prior to detachment of the spinal rod guide from the spinal rod holder.

Another embodiment relates to a spinal rod installation kit comprising a spinal screw assembly comprising a spinal screw and a spinal rod holder, the spinal rod holder defining a threaded portion and at least one seating surface; a fastener configured to threadingly engage the threaded portion of the spinal rod holder to move a spinal rod toward the at least one seating surface; a spinal rod guide comprising an upper threaded portion and a lower threaded portion, the lower threaded portion being spaced apart from the upper threaded portion and enabling continuous threading of the fastener between the lower threaded portion of the spinal rod guide and the threaded portion of the spinal rod holder; and a reduction tool configured to threadingly engage the upper threaded portion of the spinal rod guide and comprising an end portion configured to engage the fastener, the reduction tool enabling rotation of the fastener within the lower threaded portion of the spinal rod guide and the threaded portion of the spinal rod holder by way of manipulation of the reduction tool.

Another embodiment relates to a method of reducing a spinal rod, the method comprising securing a spinal rod guide assembly to a vertebral body, the spinal rod guide assembly comprising a spinal rod guide, a spinal rod holder coupled to the spinal rod guide, and a spinal screw extending through the spinal rod holder and into the vertebral body; positioning a spinal rod within the spinal rod guide; positioning a fastener onto an end of a reduction tool and positioning the end of the reduction tool and the fastener within the spinal rod guide; rotating the reduction tool such that a threaded portion of the reduction tool engages and subsequently disengages an upper threaded portion of the spinal rod guide; further rotating the reduction tool such that the fastener engages a lower threaded portion of the spinal rod guide and a threaded portion of the spinal rod holder, thereby seating the spinal rod within the spinal rod holder.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein:

FIG. 1 is a side perspective view of an embodiment of a spinal rod guide/guide assembly in accordance with the principles of the present invention;

FIG. 2 is a side view of the spinal rod guide/guide assembly of FIG. 1;

FIG. 3 is a second side view of the spinal rod guide/guide assembly of FIG. 1 taken from a side of the spinal rod guide/guide assembly that is 90° from the side view of FIG. 2;

FIG. 4 is a sectional view of the spinal rod guide/guide assembly of FIG. 1 taken along line 4-4 of FIG. 3;

FIG. 7 is an exploded perspective view of a spinal rod guide assembly according to an exemplary embodiment.

FIG. 8 is a side view of the assembly of FIG. 7 according to an exemplary embodiment.

FIG. 9 is a cross-section view of the assembly of FIG. 8 taken along line 9-9 according to an exemplary embodiment.

FIG. 15 is a cross-sectional view of a reducer used in the kit of FIG. 10 according to an exemplary embodiment.

FIG. 16 is a side view of a removal tool according to an exemplary embodiment.

FIG. 17 is a perspective view of a guide assembly according to an exemplary embodiment.

FIG. 18 is a perspective view of a portion of the guide assembly of FIG. 17 according to an exemplary embodiment.

FIG. 19 is a perspective view of a portion of the guide assembly of FIG. 17 according to an exemplary embodiment.

FIG. 20 is a cross sectional view of the guide assembly of FIG. 17 according to an exemplary embodiment.

FIG. 25 is a perspective view of the guide assembly of FIG. 17 with a spinal rod in a second initial position and a reduction tool according to an exemplary embodiment.

FIG. 26 is a cross-sectional view of the guide assembly, spinal rod, and reduction tool of FIG. 25 according to an exemplary embodiment.

FIG. 27 is a cross-sectional view of a portion of the guide assembly and spinal rod of FIG. 25 according to an exemplary embodiment.

FIG. 28 is a cross-sectional view of a portion of the guide assembly, spinal rod, and reduction tool of FIG. 25 according to an exemplary embodiment.

FIG. 29 is a cross-sectional view of a portion of the guide assembly, spinal rod, and reduction tool of FIG. 25 according to an exemplary embodiment.

Like reference numerals indicate the same or similar parts throughout the several figures.

Figure 5:
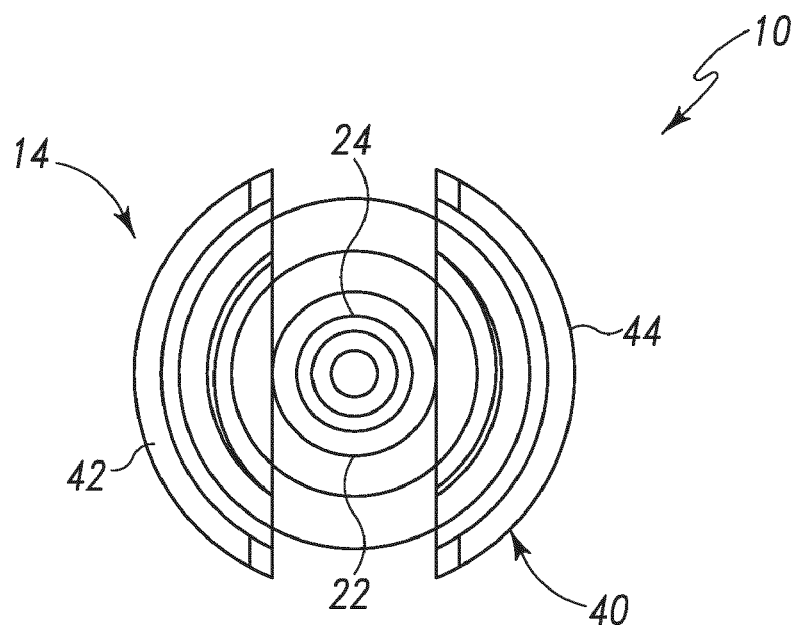
FIG. 5 is a top plan view of the spinal rod guide/guide assembly of FIG. 1 taken along line 5-5 of FIG. 3.
Figure 6:
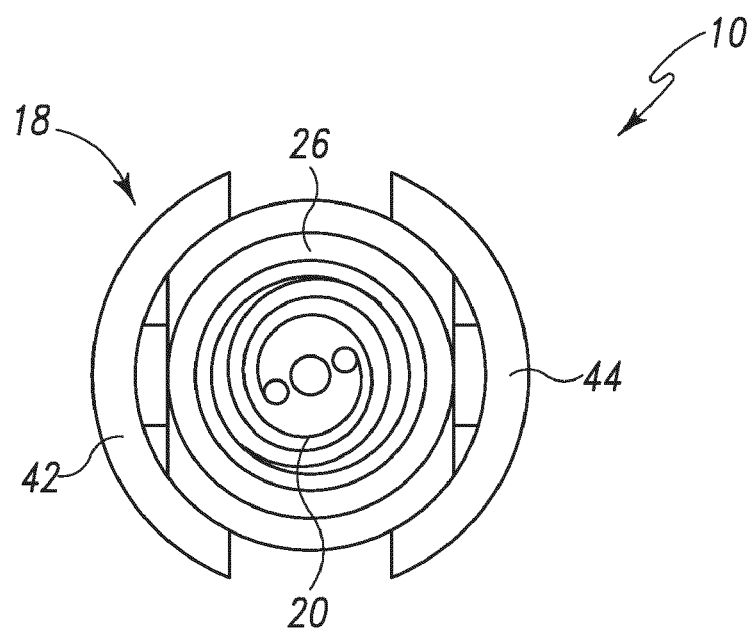
FIG. 6 is a bottom plan view of the spinal rod guide/guide assembly of FIG. 1 taken along line 6-6 of FIG. 3.

A description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF EXEMPLARY EMBODIMENTS

FIGS. 1-6 depict various views of a spinal rod guide/guide assembly generally designated 10 for the introduction, placement and securing of a spinal rod relative to vertebrae of a patient. The spinal rod guide assembly 10 is defined by a vertebral bone screw assembly 12 that is particularly, but not necessarily, a pedicle bone screw assembly (pedicle screw assembly) 12 and a spinal rod guide component 14. The spinal rod guide 10 is defined by the spinal rod guide component 14. The spinal rod guide/guide assembly 10 is made from titanium, stainless steel or another biocompatible material.

In one form, the spinal rod guide 10 may be considered as the spinal rod guide component 14 and, as such, the terms are interchangeable. In another form, the spinal rod assembly 10 may be considered as the spinal rod guide component 14 and the pedicle bone screw assembly 12 and, as such, the terms are interchangeable.

The pedicle bone screw assembly 12 is formed of a pedicle screw 16 and a spinal rod holder or connector 18. The pedicle screw 16 is defined by a threaded body, shank or shaft 20 with a rounded head 22. A configured socket 24 is provided in the screw head 22. The spinal rod connector 18 is situated on the pedicle screw head 22. The spinal rod connector 18 and the pedicle screw head 22 are connected such that the spinal rod connector 18 can swivel or rotate about the pedicle screw head 22. This allows the spinal rod connector 18 to assume various orientations relative to the pedicle screw 16 in order to accommodate a spinal rod (not shown).

The spinal rod connector 18 is defined by a generally tulip-shaped body 26 having a lower opening 28 that is configured to allow the pedicle screw shaft 20 to extend therethrough but to retain the pedicle screw head 22. The pedicle screw head 22 is thus sized to be rotatably captured by the body 26. By virtue of its shape, the body 26 has a first side or side member 30 and a second side or side member 32 extending from a base 27 of the body 26. The first and second side members 30 and 32 are separated from each other on one side by a first slot 34 and on another side by a second slot 36. The first and second side members 30 and 32 are essentially situated diametrically opposite one another on the body 26. The first and second slots 34 and 36 are likewise situated diametrically opposite one another on the body 26 and are sized and configured to receive a spinal rod therein (not shown). An upper inside surface of the first side member 30 includes threads 31, while an upper inside surface of the second side member 32 also includes threads 33. The threads 31, 32 are configured for receiving a threaded spinal rod connector screw (not shown) for securing the spinal rod (not shown) within the spinal rod connector 18.

The spinal rod guide component 14 is defined by a first elongated arc portion or side 42 and a second elongated arc portion or side 44 that together defined an elongated guide tube 40. The first and second elongated arc portions 42 and 44 are separated from one another on one side by a first elongated slot 50 and on another side by a second elongated slot 52. The first and second elongated arc portions 42 and 44 are essentially situated diametrically opposite one another on the guide tube 40. The first and second elongated slots 50 and 52 are likewise situated diametrically opposite one another on the guide tube 40 and are sized and configured to receive a spinal rod therein (not shown) and allow the spinal rod to slide down into the first and second slots 34 and 36 of the spinal rod connector 18. In this manner, a spinal rod (not shown) is guided from an upper end 48 of the tube into the spinal rod connector 18, and specifically into the first and second slots 34, 36 of the spinal rod connector 18, via the first and second elongated slots 50, 52.

The guide tube 40 moreover defines a tubular bore 46 that extends from the upper end 48 to the spinal rod holder body 26. The tubular bore 46 is sized to allow a pedicle screw driver to be received in the screw socket 24 and for a spinal rod holder screw (not shown) to be placed into the spinal rod connector 18 and be threadedly received by the first and second inner threads 31, 33 of the first and second sides 30, 32 of the spinal rod connector body 26 in order to secure a spinal rod (not shown) therein. Other components may also be placed through the guide tube 40.

The spinal rod guide component 14 is shown having a first taper 54 on a lower end of the first elongated arc portion 42 of the guide tube 40 and a second taper 56 on a lower end of the second elongated arc portion 44 of the guide tube 40. It should be appreciated that such tapers are not necessary.

In one embodiment, the spinal rod guide component 14 of the spinal rod guide assembly 10 and, more particularly, the guide tube 40 is formed with or made to the spinal rod holder 18. Particularly, the lower end of the first elongated arc portion 42 of the guide tube 40 is formed with or made to the second side 32 of the spinal rod holder body 26 while the lower end of the second elongated arc portion 44 of the guide tube 40 is formed with or made to the first side 30 of the spinal rod holder body 26. A first junction or juncture 55 is defined between the lower end of the first elongated arc portion 42 of the guide tube 40 and the second arc portion 32 of the spinal rod holder body 26. The first juncture 55 is scored or otherwise fashioned such that the first elongated arc portion 42 can break away or snap off from the second side 32. Likewise, a second junction or juncture 57 is defined between the lower end of the second elongated arc portion 44 of the guide tube 40 and the first side 30 of the spinal rod holder body 26. The second juncture 57 is scored or otherwise fashioned such that the second elongated arc portion 44 can break away or snap off from the first side 30. In this manner, when the spinal rod is set and secured in the spinal rod holder 18, the spinal rod guide component 14 may be removed.

In another embodiment, the spinal rod guide 14 may be attached or attachable to a spinal rod connector 18 by threads or another means. Particularly, the lower end of the first elongated arc portion 42 of the guide tube 40 may include threads that are threadedly received by threads on the second end 32 of the spinal rod holder body 26. Likewise, the lower end of the second elongated arc portion 44 of the guide tube 40 may include threads that are threadedly received by threads on the first end 30 of the spinal rod holder body 26. Thus, when the spinal rod is set and secured in the spinal rod holder 18, the spinal rod guide 14 may be threadedly removed from the spinal rod holder 18.

The inside surface, interior or inner lumen of the first and second arc portions (guide tube) may also include threads or threading along their (its) length. This allows a locking cap for the spinal rod holder to be threaded down the guide tube such that the locking cap pushes the spinal rod down into the spinal rod holder along with the locking cap to secure the spinal rod into the spinal rod holder. This also provides a manner to reduce a spondylolisthesis condition.

The present spinal rod guide/guide assembly allows easy installation of a spinal rod into one and/or a plurality of spinal rod connectors of pedicle screws and the fixing thereof utilizing a minimally invasive surgical technique.

FIGS. 7-16 show a spinal rod guide/guide assembly according to various exemplary embodiments. Referring to FIGS. 7-9, a spinal rod guide assembly 110 (e.g., a guide assembly, a spinal fixation assembly, etc.) is shown and includes a screw assembly 112 (e.g., a bone screw assembly such as a vertebral bone screw assembly) and a spinal rod guide component 114 (e.g., a spinal rod guide, etc.). Assembly 110 is similar to spinal rod guide assembly 10 shown in FIGS. 1-6, and may include any of the features described with respect to spinal rod guide assembly 10 and FIGS. 1-6.

Spinal rod guide 114 includes a pair of arcuate members, or tabs 142, 144 (e.g., flanges, extensions, arc members, etc.) that define a pair of longitudinal slots 150, 152. Tabs 142, 144 define a generally cylindrical shaped cross-section and have a longitudinal axis 151 (see FIG. 9). Tab 142 includes a pair of transverse slots, or recesses, 162, 166. Similarly, tab 144 includes a pair of transverse slots, or recesses 160, 164. The length of tabs 142, 144, the width of slots 150, 152, are the size and position of recesses 160-166 may be varied according to various alternative embodiments. Referring to FIG. 8, tabs 142, 144 may be fixedly coupled to connector 118 via one or more welds 165 (e.g., laser welds, ultrasonic welds, resistance welds, etc.). For example, according to one embodiment, each tab 142, 144 is coupled to connector 118 via three laser welds, although more or fewer welds, or different types of welding techniques (e.g., resistance welding, ultrasonic welding, etc.) may be used in alternative embodiments. As discussed in greater detail below, welds 165 provide a rigid connection between tabs 142, 144 that may later be sheared, or broken, via application of torque to tabs 142, 144. According to other exemplary embodiments, tabs 142, 144 may be coupled to connector 118 by a single continuous weld, adhesive, or a cold-formed bond. Alternatively, tabs 142, 144 may be integrally formed with connector 118.

According to an exemplary embodiment, screw assembly 112 includes a screw 116 (e.g., a pedicle screw) and a spinal rod holder or connector 118. Connector 118 includes a body 126 and a securing member 117. Securing member 117 threadingly engages the interior of body 126 to captively secure screw 116 in a rotatable fashion to connector 118. As shown in FIG. 8, body 126 may have a tulip shape, as also discussed with respect to connector 18. For example, body 126 may include a bulge portion 119 (see FIG. 8) that has a diameter greater than the diameter of the top and/or bottom of body 126. In some embodiments, a portion of connector 118 (e.g., bulge portion 119) has a diameter greater than the diameter defined by tabs 142, 144 (e.g., a cylinder encompassing tabs 142, 144). This may minimize the required skin incision and reduce muscle trauma relative to more invasive systems. Also, the tulip-shaped body is configured to allow a greater degree of freedom for the insertion angle and orientation of connector 118. As shown in FIG. 9, connector 118 is configured to receive a spinal rod 121. Spinal rod 121 may be made of any appropriate material, and have any diameter and length to suit a particular application.

As also discussed with respect to FIGS. 1-6, screw 116 is configured to be secured to a bone (e.g., a vertebral body) of a patient. Screw 116 is captively held by connector 118. Connector 118 is in turn configured to receive spinal rod 121, which is secured to connector 118 via a fastener (not shown). Spinal rod 121 may be guided into position using spinal rod guide 114, such that spinal rod 121 may be slid down within slots 150, 152 and between tabs 142, 144. Once in position, the fastener (not shown) is tightened to secure spinal rod 121 in place within connector 118.

In some situations, various factors (spinal irregularities, spondylolisthesis, etc.) may prevent the proper "seating" of spinal rod 121 within connector 118. In other words, in some cases spinal rod 121 may not be positionable adjacent to surface 115 (see FIG. 7) of connector 118, and will instead be positioned at some distance (e.g., 1 mm, 5 mm, etc.) from surface 115 and a "fully seated" position. In such instances, it may be necessary to "reduce" the spinal rod to the fully seated position, as discussed in greater detail below.

Figure 10:
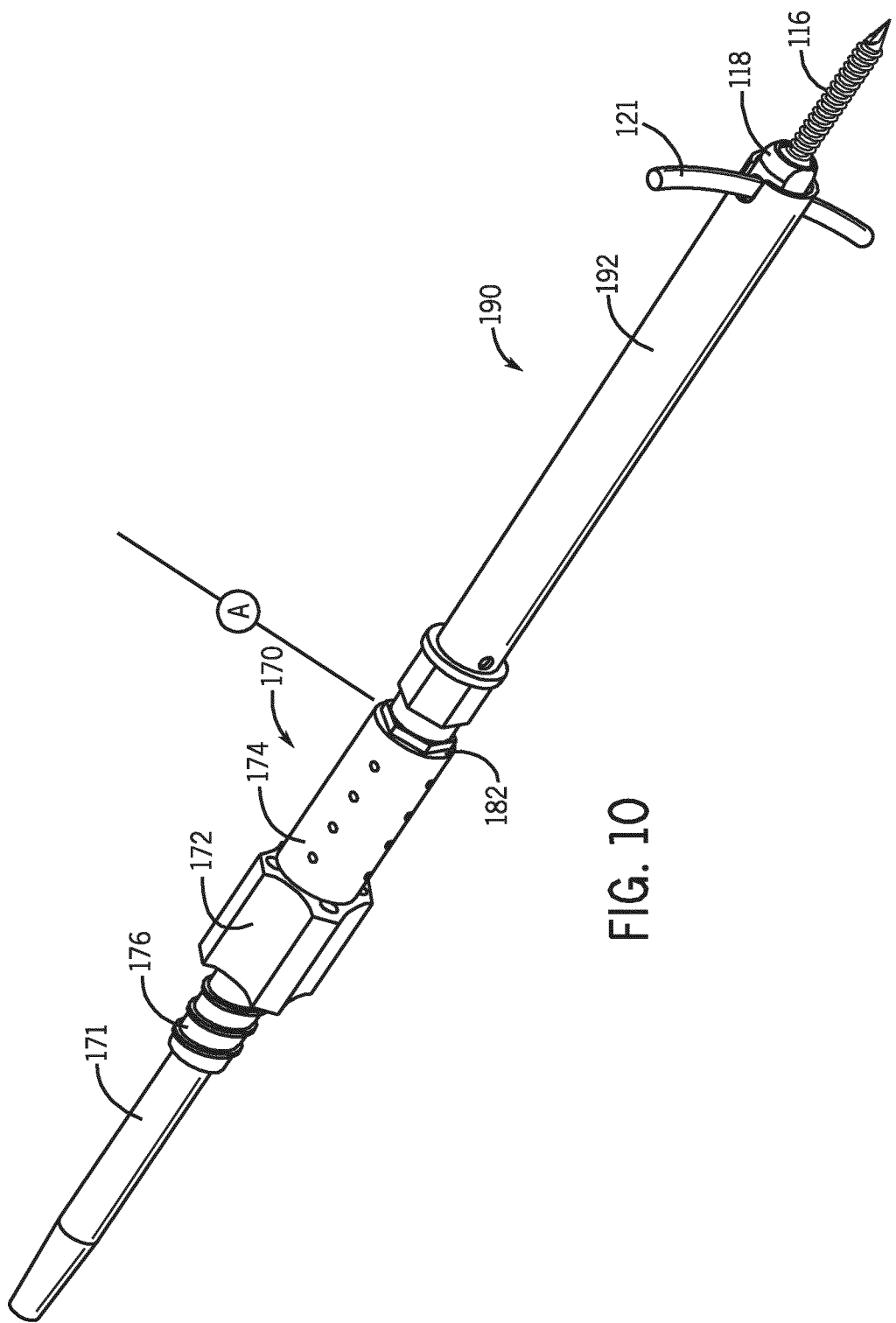
FIG. 10 is a perspective view of a reduction kit according to an exemplary embodiment.
Figure 11:
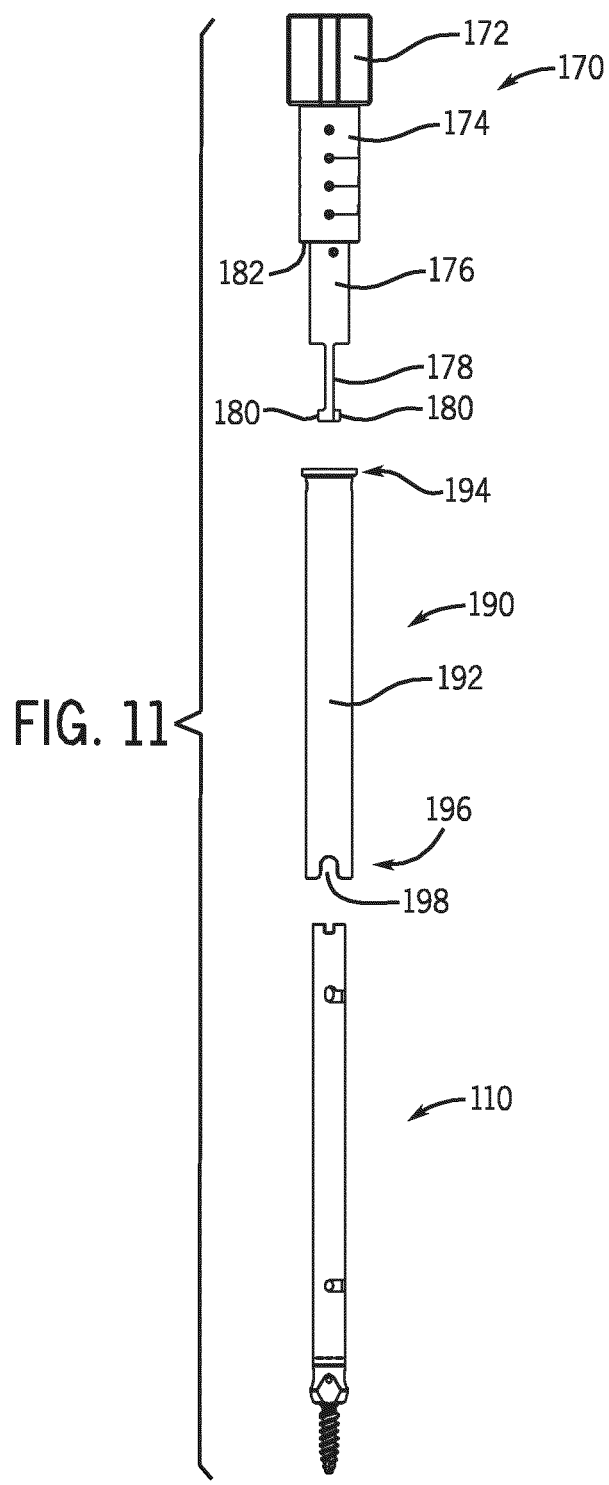
FIG. 11 is an exploded side view of the kit of FIG. 10 according to an exemplary embodiment.
Figure 12:
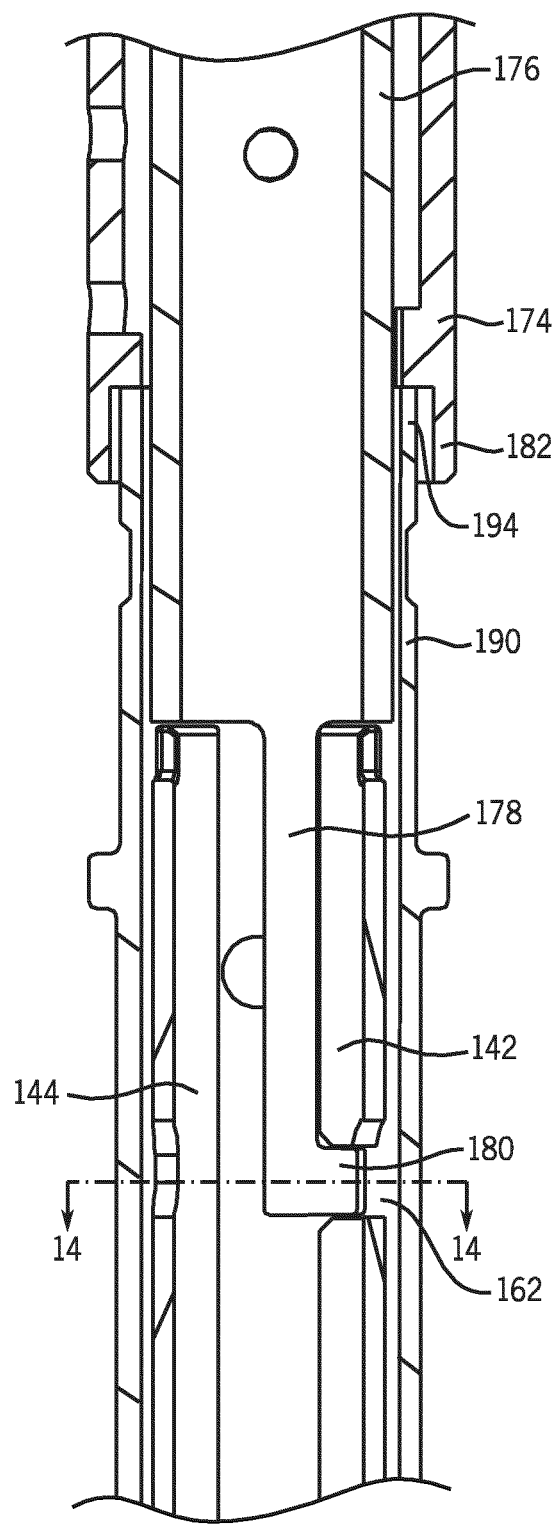
FIG. 12 is a cross-sectional view of a portion of the kit of FIG. 10 according to an exemplary embodiment.
Figure 13:
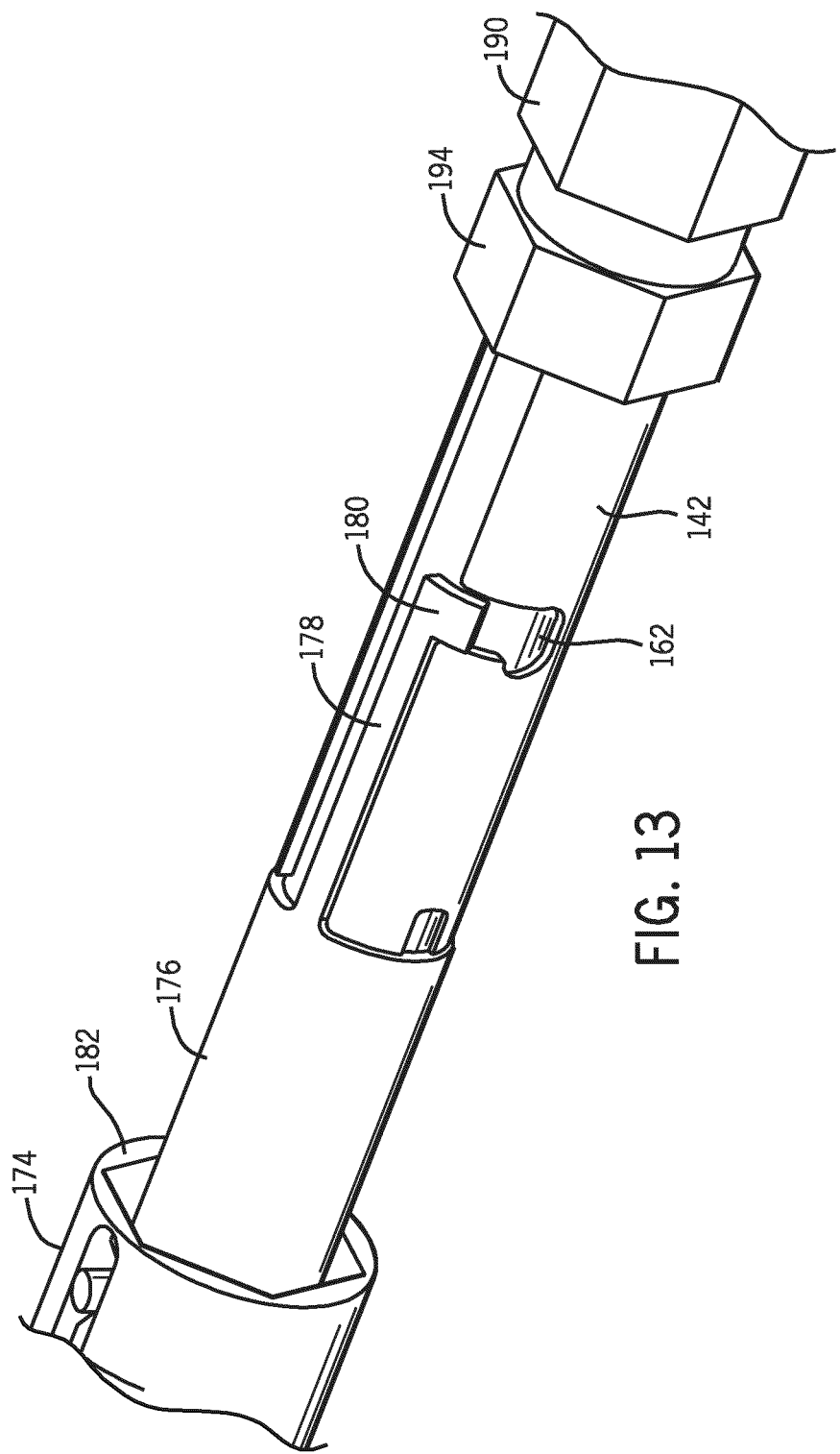
FIG. 13 is a perspective view of a portion of the kit of FIG. 10 showing a reducer separated from a spacer according to an exemplary embodiment.
Figure 14:
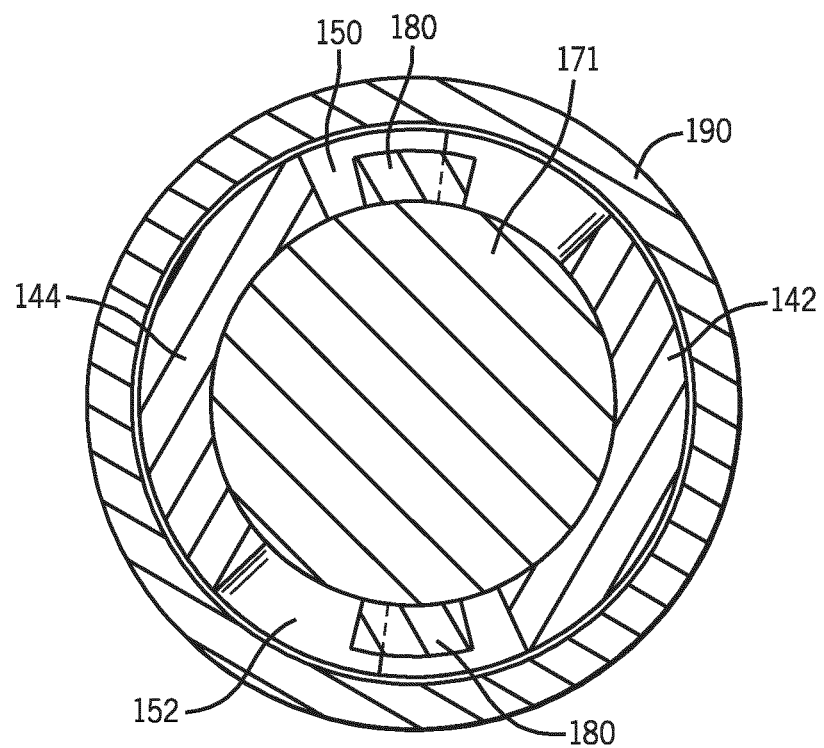
FIG. 14 is a cross-sectional view of the kit of FIG. 10 taken along line 14-14 of FIG. 12 according to an exemplary embodiment.

Referring now to FIGS. 10-16, various components and methods for reducing a spinal rod are showing according to various exemplary embodiments. As shown in FIG. 11, a kit 169 for reducing a spinal rod is shown according to an exemplary embodiment, and includes a guide assembly 110, a spacer 190, and a reducer 170. As discussed in detail herein, kit 169 is usable to fully reduce a spinal rod such as spinal rod 121 to a fully seated position. In some embodiments, kit 169 is configured to reduce spinal rod 121 a maximum of 20 mm. According to various other embodiments, kit 169 may be configured to provide reduction of greater or lesser amounts.

Referring to FIGS. 10-13, spacer 190 (e.g., a countertorque wrench or member, etc.) is a generally cylindrical member having a hollow, cylindrical body 192, a first end 194, and a second end 196. End 196 includes a pair of notches or recesses 198 configured to receive spinal rod 121 and prevent rotation of spinal rod 121 relative to spacer 190. End 194 may include a hexagonal or other shaped portion configured to prevent relative rotation between spacer 190 and one or more portions of reducer 170.

According to an exemplary embodiment, reducer 170 includes a pair of outer members shown as a knob 172 and a sleeve 174, and an inner member shown as shaft 176. Reducer 170 is configured to engage spacer 190 and guide assembly 110 such that reducer 170 enables a user to reduce spinal rod 121 relative to guide assembly 110.

Referring to FIGS. 11 and 15, knob 172 is threadingly coupled to shaft 176 such that rotation of knob 172 causes a corresponding movement (e.g., longitudinal or translational movement) of shaft 176 relative to knob 172. Knob 172 may take any appropriate shape and/or size and be made of any appropriate material.

Sleeve 174 is slidably positioned on shaft 176. According to one embodiment, sleeve 174 is configured such that shaft 176 may freely slide longitudinally within sleeve 174, but shaft 176 may not rotate relative to sleeve 174. For example, a pin or other extension may extend from the exterior of shaft 176 and be received within a longitudinally positioned slot on sleeve 174 such that longitudinal, but not rotational, relative movement is permitted between sleeve 174 and shaft 176. Thus, as knob 172 is rotated, shaft 176 moves, or translates, in a longitudinal manner relative to sleeve 174.

According to one embodiment, shaft 176 of reducer 170 includes a pair of extensions 178, with each extension 178 including a tab 180. Extensions 178 are formed in an arcuate fashion such that the curvature of extensions 178 and tabs 180 generally matches the curvature of tabs 142, 144. Furthermore, the outside diameter of extensions 178 is configured to provide a snug, but sliding fit of extensions 178 within the interior of spacer 190 (which may have a cylindrically-shaped interior). Furthermore, in order to prevent inward deflection of extensions 178 and/or tabs 142, 144, a cylindrical guide rod 171 (e.g., a switching stick) may be introduced within tabs 142, 144 (see FIG. 10). As discussed in greater detail below, this may facilitate maintaining a proper interface between extensions 178/tabs 180 and tabs 142, 144.

In order to reduce spinal rod 121, spacer 190 is slid over guide assembly 110 such that notches 198 receive spinal rod 121. If desired, center guide or switching stick 171 may be introduced within tabs 142, 144. Reducer 170 is positioned such that extensions 178 slide between tabs 142, 144 (e.g., within longitudinal slots 150, 152) until extensions 178 may be rotated such that tabs 180 are received within recesses 160, 162 in tabs 142, 144. According to one embodiment, tabs 180 and recesses 160, 162 have complimentary shapes such that longitudinal movement of extensions 178 and tabs 180 causes a corresponding longitudinal movement of tabs 142, 144, and in turn, connector 118. In other embodiments, tabs 180 and recesses 160, 162 may provide a bayonet-type connection. When reducer 170 is positioned, end 182 of sleeve 174 engages end 194 of spacer 190 so as to prevent relative longitudinal or rotational movement between sleeve 174 and spacer 190. Furthermore, according to one embodiment, sleeve 174 and shaft 176 may be keyed to one another so as to permit longitudinal, but not rotational, movement between the components.

With reducer 170 and spacer 190 in proper position, knob 172 of reducer 170 may be rotated (e.g., in a clockwise fashion) upon shaft 176, causing shaft 176 to move upward (e.g., away from a patient's body) through knob 172 and sleeve 174, thereby pulling spinal rod guide assembly 110 upward in a corresponding manner due to the engagement of tabs 180 with recesses 160, 162. Thus, as knob 172 is rotated, the distance between connector 118 and line A shown in FIG. 10 is decreased (in effect, pulling the bone screw and the vertebral body toward the user/physician). At the same time, spacer 190, due to its engagement at end 194 with sleeve 174 and its engagement at end 196 with spinal rod 121, maintains a constant distance between spinal rod 121 and line A shown in FIG. 10. In other words, as knob 172 is rotated, shaft 176 and tabs 142, 144 move upward within spacer 190, thereby moving connector 118 toward spinal rod 121, which is held in place by spacer 190. Upon further rotation of knob 172, connector 118 will eventually be moved a sufficient distance relative to spinal rod 121 such that spinal rod 121 is in a fully seated position and may be fastened into place.

Providing a reduction kit such as kit 169 provides advantages over more conventional reduction techniques. For example, tabs 142, 144 serve the dual purposes of guiding spinal rod 121 into position, and enabling a user to reduce spinal rod 121 if necessary, thereby reducing the number of tools, fixtures, etc., required for a spinal fixation procedure. Furthermore, because the reduction components are all contained within spacer 190, the procedure is minimally invasive and does not require additional access space, etc., in order to reduce the spinal rod.

Referring now to FIG. 16, a removal tool 200 is shown according to an exemplary embodiment. As shown in FIG. 16, tool 200 includes a handle 202, a generally cylindrical shaft 204 extending from handle 202, and a number of pins, or extensions, 206, 208, extending from shaft 204. According to one embodiment, extensions 206, 208 are sized and located such that when tool 200 is inserted into guide assembly 110, extensions 206, 208 may be received within recesses 160-166. As such, rotation of tool 200 will generate a corresponding torque on tabs 142, 144. In some embodiments, recesses 160-166 may be provided at an angle other than 90 degrees relative to the length of tabs 142, 144 such that as tool 200 is rotated, the tool tends move "upward" along the recesses. As such, both a rotational and longitudinal force may be applied to the tabs. Upon application of sufficient torque/force, tabs 142, 144 are configured to separate (e.g., break away, shear from, etc.), connector 118, such that tabs 142, 144 may be removed from a procedural area. While in some embodiments tabs 142, 144 are removed by applying a torque via tool 200, according to other embodiments, other methods of removing tabs 142, 144 may be used, including pulling tabs 142, 144 straight off (e.g., along the longitudinal axis of the tabs), bending the tabs inward/outward, etc. In some embodiments, tabs 142, 144 are moved in a non-bending manner during removal (e.g., via rotational about their longitudinal axis, via puling along their longitudinal axis, a combination thereof, etc.).

Tool 200 and guide assembly 110 provide an easy and minimally invasive means for removing tabs 142, 144 from connector 118. In contrast to other techniques, which may require bending, rocking, or other manipulation of various components against the surrounding muscle, bone, tissue, etc., tool 200 is configured to be received within tabs 142, 144, such that in one embodiment rotation of tool 200 is the only force/torque required to break away tabs 142, 144 from connector 118. Furthermore, no additional tools, etc. are required to break away and remove tabs 142, 144.

The systems and methods described herein provide may provide many benefits over more traditional means of installing and reducing spinal rods and similar components. For example, tabs 142, 144 act as rigid fenestra without the concern of the tabs falling off during a procedure, due to the rigid, laser-welded connection of the tabs to the spinal rod holder. Further, the components provide a minimally invasive technique that minimizes the trauma to the patient and the length of the procedure (e.g., as a result of the easy removal feature of the tabs, etc.).

Referring now to FIGS. 17-33, various components and methods for reducing a spinal rod are showing according to various exemplary embodiments. Referring to FIGS. 17-20, a spinal rod guide assembly 310 (e.g., a guide assembly, a spinal fixation assembly, etc.) is shown and includes a screw assembly 312 (e.g., a bone screw assembly such as a vertebral bone screw assembly, etc.) and a spinal rod guide component 314 (e.g., a spinal rod guide, etc.). Assembly 310 may share certain features with spinal rod guide assemblies 10 and 110, and may include any of the features discussed in connection therewith.

Spinal rod guide 314 includes a pair of arcuate members, or tabs 342, 344 (e.g., flanges, extensions, arc members, etc.) that define a pair of longitudinal slots 350, 352 and a central bore 353. Tabs 342, 344 define a generally cylindrical shaped cross-section and have a longitudinal axis 351 (see FIG. 17). Tab 342 includes a pair of transverse slots, or recesses 360, 362. Similarly, tab 344 includes a pair of transverse slots, or recesses 360, 362. The length of tabs 342, 344, the width of slots 350, 352, and the size and position of recesses 360, 362 may be varied according to various alternative embodiments.

Referring to FIGS. 18 and 19, tabs 342, 344 terminate at an upper end at a top 370 and terminate at a lower end at a spinal rod holder 318. Tabs 342, 344 may be detachably coupled to spinal rod holder 318 via one or more joints shown as welds 363 (e.g., laser welds, ultrasonic welds, resistance welds, etc.). For example, according to one embodiment, each tab 342, 344 is coupled to spinal rod holder 318 via one continuous weld, although more welds, or different types of welding techniques (e.g., resistance welding, ultrasonic welding, etc.) may be used in alternative embodiments. As discussed in greater detail below, welds 363 provide a rigid connection between tabs 342, 344, and spinal rod holder 318. According to other exemplary embodiments, tabs 342, 344 may be coupled to spinal rod holder 318 via three laser welds that may later be sheared, or broken, via application of torque to tabs 342, 344, although more or fewer welds, or different types of joining techniques (e.g., resistance welding, ultrasonic welding, adhesives, or a cold-formed bond, etc.) may be used in alternative embodiments. Alternatively, tabs 342, 344 may be integrally formed with spinal rod holder 318.

Figure 32:
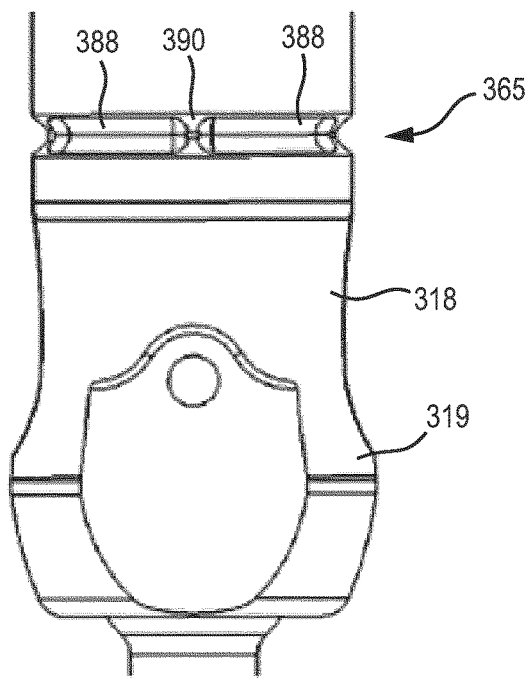
FIG. 32 is a front view of a portion of a spinal guide assembly according to an exemplary embodiment.
Figure 33:
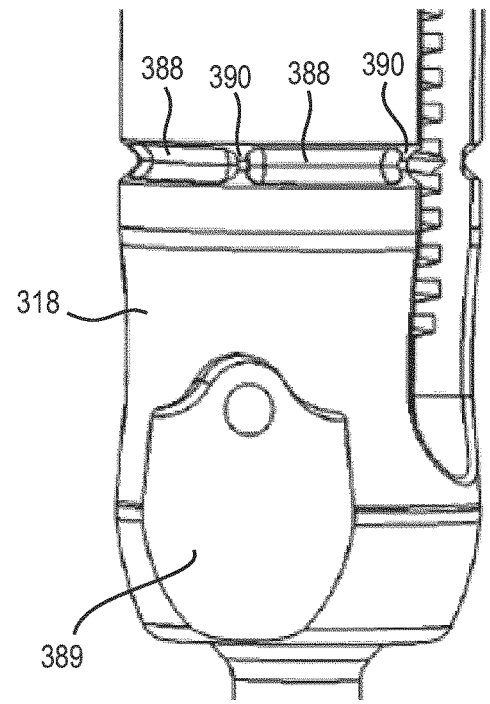
FIG. 33 is a rotated front view of a portion of a spinal guide assembly according to an exemplary embodiment.

According to one embodiment, spinal rod holder 318 includes a pair of upstanding portion 367, 369 that extend upward and are coupled to tabs 342, 344 by welds 363. Each of upstanding portions 367, 369 includes a fracture joint, or joint 365 that defines a plurality of struts 390 (see FIGS. 32-33) extending between intermediate threaded portion 376 and lower threaded portion 380 along longitudinal axis 351. For example, as shown in FIGS. 32-33, each tab 342, 344 may be joined to upstanding portions 367, 369 by way of three spaced apart struts 390, with grooves, or recesses 388 being located between adjacent struts. Grooves 388 may be machined grooves. In other embodiments, more or fewer struts may be utilized, and the shape and/or size of the struts may be varied to suit a particular application. Grooves 338 and struts 390 are configured to provide the desired strength and fracture properties between spinal rod guide 314 and the portion of spinal rod holder 318 above joint 365 from the remainder of spinal rod holder 318. The size and number of struts 390 enable the amount of torque required to detach spinal rod guide assembly 314 from spinal screw assembly 312 to be controlled. Additionally, the design of the struts and grooves provides greater column support/strength for tabs 342, 344 relative to other coupling methods while maintaining a consistent removal/fracture torque.

Top 370 is a generally cylindrical and/or polygonal member, or ring, that extends between tabs 342, 344 in a fully closed fashion to join the ends thereof. Top 370 defines an upper threaded portion 372 of spinal rod guide 314 which, as discussed in greater detail below, is configured to engage a threaded portion 384 of a reduction tool 382 (see FIG. 22). The opposite ends of tabs 342, 344 terminate at weld 363 above an intermediate threaded portion 376 of spinal rod guide 318. In one embodiment, upper threaded portion 372 has a larger thread pitch than intermediate threaded portion 376 to provide different types of adjustment (e.g., coarse vs. fine) depending on which threads are used. For example, for initial reduction, coarser threads may be used to provide a faster reduction, while for final reduction adjustments, finer threads may be desirable to enable finer adjustments.

According to an exemplary embodiment, screw assembly 312 includes a screw 316 (e.g., a pedicle screw, etc.) and spinal rod holder or spinal rod holder 318. Spinal rod holder 318 includes a body 326, upstanding portions 367, 369, and a securing member 329. Securing member 329 captively secures screw 316 in a rotatable fashion to spinal rod holder 318. As shown in FIG. 32, body 326 may have a tulip shape, as also discussed with respect to spinal rod holder 18. For example, body 326 may include a bulge portion 319 (see FIG. 32) that has a diameter greater than the diameter of the top and/or bottom of body 326. In some embodiments, a portion of spinal rod holder 318 (e.g., bulge portion 319) has a diameter greater than the diameter defined by tabs 342, 344 (e.g., a cylinder encompassing tabs 342, 344). This may minimize the required skin incision and reduce muscle trauma relative to more invasive systems. Also, the tulip-shaped body is configured to allow a greater degree of freedom for the insertion angle and orientation of spinal rod holder 318. One or more flat portions 389 (see, e.g., FIGS. 32-33) may be formed on spinal rod holder 318 and be usable, for example, as a gripping and/or engagement surface for one or more tools, etc. As shown in FIG. 29, spinal rod holder 318 is configured to receive a spinal rod 321. Spinal rod 321 may be made of any appropriate material, and have any diameter and length to suit a particular application.

As shown in FIG. 20, intermediate threaded portion 376 and lower threaded portion 378 of spinal rod holder 318 form a nearly continuous threaded portion having a substantially constant thread pitch, such that a fastener such as fastener 317 can be continuously threaded along intermediate threaded portion 376 and lower threaded portion 380 of spinal rod holder 318. As discussed above, spinal rod guide assembly 310 includes three separate threaded portions, including upper threaded portion 372 of spinal rod guide 314, intermediate threaded portion 376 of spinal rod holder 318, and lower threaded portion 380 of spinal rod holder 318.

Screw 316 is configured to be secured to a bone (e.g., a vertebral body, etc.) of a patient. Screw 316 is captively held by spinal rod holder 318. Spinal rod holder 318 is in turn configured to receive spinal rod 321, which is secured to spinal rod holder 318 via fastener 317 (e.g., a locking collar, screw, etc.). Spinal rod 321 may be guided into position using spinal rod guide 314, such that spinal rod 321 may be slid down within slots 350, 352 and between tabs 342, 344. Once in position, fastener 317 is tightened to secure spinal rod 321 in place within spinal rod holder 318.

In some situations, various factors (e.g., spinal irregularities, spondylolisthesis, etc.) may prevent the proper "seating" of spinal rod 321 within spinal rod holder 118. In other words, in some cases spinal rod 321 may not be positionable adjacent to a seating surface 315 (see FIG. 19) of connector 318, and will instead be positioned at some distance (e.g., 1 mm, 5 mm, etc.) from surface 315 and a "fully seated" position. In such instances, it may be necessary to "reduce" the spinal rod to the fully seated position, as discussed in greater detail below.

Figure 22:
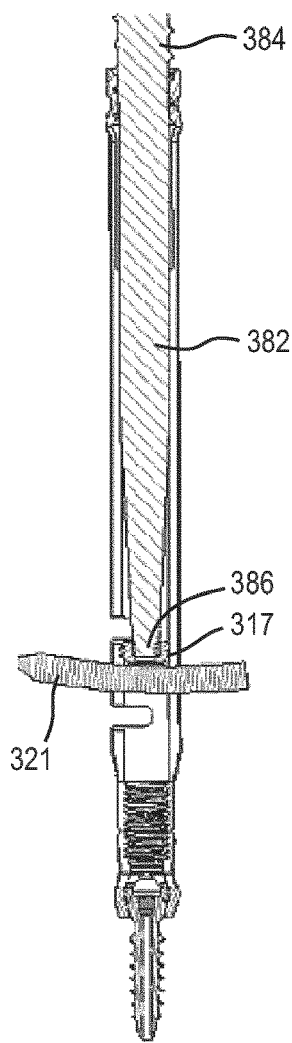
FIG. 22 is a cross-sectional view of the guide assembly, spinal rod, and reduction tool of FIG. 21 according to an exemplary embodiment.
Figure 21:
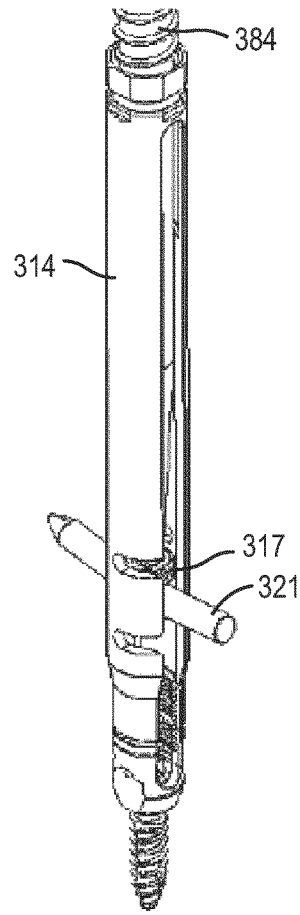
FIG. 21 is a perspective view of the guide assembly of FIG. 17 with a spinal rod in a first initial position and a reduction tool according to an exemplary embodiment.
Figure 23:
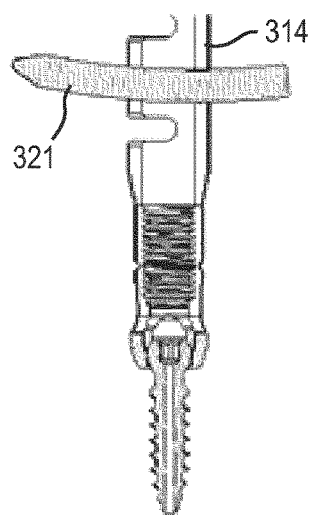
FIG. 23 is a cross-sectional view of a portion of the guide assembly and spinal rod of FIG. 21 according to an exemplary embodiment.
Figure 24:
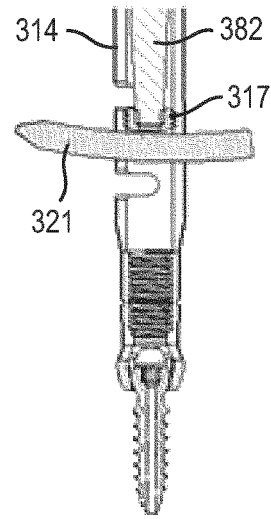
FIG. 24 is a cross-sectional view of a portion of the guide assembly, spinal rod, and reduction tool of FIG. 21 according to an exemplary embodiment.

Referring now to FIGS. 21-31, various components and methods for reducing a spinal rod (e.g., to restore one or more vertebral bodies or other parts to a substantially normal anatomical position, etc.) are shown according to various exemplary embodiments. As shown in FIGS. 21-22, a tool 382 usable to reduce a spinal rod such as spinal rod 321 may be a generally elongated, cylindrical member that tapers along all or a portion of its length (e.g., to facilitate insertion and/or removal of the tool). Tool 382 includes a threaded portion 384 spaced apart from an end portion 386. Threaded portion 384 is configured to threadingly engage upper threaded portion 372 of spinal rod guide 314, and end portion 386 is configured to engage fastener 317 in a rotationally fixed fashion (e.g., by way of correspondingly shaped hex-heads/sockets, etc.) such that rotation of tool 382 causes a corresponding rotation of fastener 317.

According to an exemplary embodiment, tool 382 and assembly 310 are configured such that threaded portion 384 is threadingly received by upper threaded portion 372. Threaded portion 384 is spaced apart from end 386 such that threaded portion 384 disengages from upper threaded portion 372 prior to fastener 317 engaging intermediate threaded portion 376. The spacing between the various threaded portions and the length of tool 382 may be varied to suit a particular application. This configuration allows a user to reduce a spinal rod a first amount through the engagement of tool 382 and upper threaded portion 372, and to reduce the spinal rod a second amount through the engagement of fastener 317 and intermediate threaded portion 376 and lower threaded portion 380. Upper threaded portion 372 and intermediate threaded portion 376 provide supplemental reduction capabilities in addition to the reduction enabled by lower threaded portion 380.

In use, spinal screw 316 is fastened to a vertebral body, and spinal rod 321 is slid into an initial position as discussed above. Referring to FIGS. 21-24, the initial position of spinal rod 321 may be such that fastener 317 is above, or outside of, intermediate threaded portion 376 of spinal rod holder 318. As such, threaded portion 384 of tool 382 may be threaded into upper threaded portion 372 of spinal rod guide 314. As tool 382 is rotated, tool 382 (and, therefore, fastener 317) moves relative to spinal rod guide 314 such that fastener 317 pushes spinal rod 321 toward intermediate threaded portion 376. Upper threaded portion 372, in combination with the instrumentation of tool 382 and threaded portion 384, provides a greater amount of reduction of the spinal rod relative to more traditional techniques.

Figure 30:
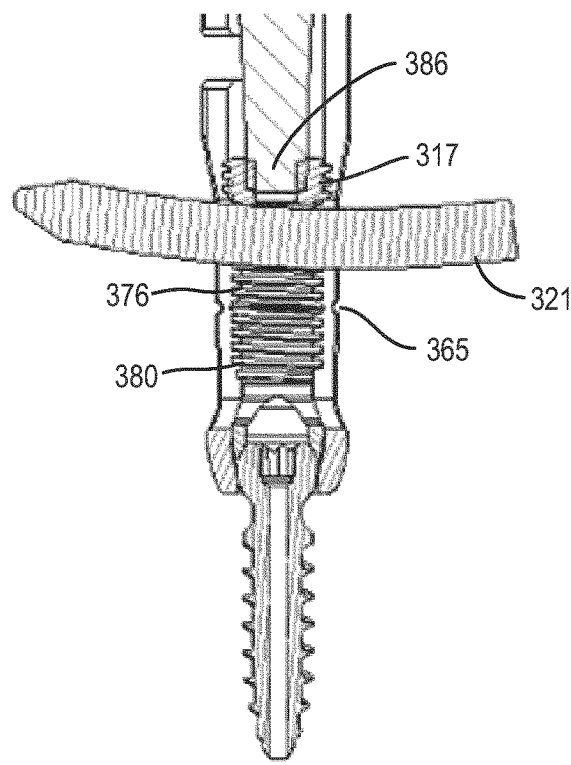
FIG. 30 is a cross sectional view of a portion of a guide assembly, spinal rod, and reduction tool according to an exemplary embodiment.
Figure 31:
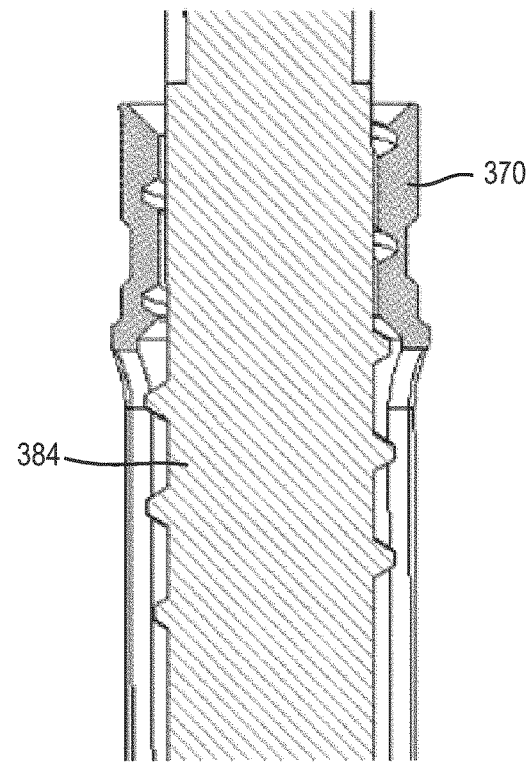
FIG. 31 is a cross sectional view of a portion of the guide assembly and reduction tool of FIG. 30 according to an exemplary embodiment.

Referring to FIGS. 30-31, just prior to fastener 317 engaging intermediate threaded portion 376 (see FIG. 30), threaded portion 384 of tool 382 disengages upper threaded portion 372 (see FIG. 31). This disengagement/engagement feature prevents simultaneous threading on both upper threaded portion 372 and intermediate threaded portion 376. Fastener 317 may then be threadingly moved within intermediate threaded portion 376 and lower threaded portion 380 to further reduce spinal rod 321 toward a seated position (e.g., proximate seating surface 315), as discussed in greater detail below.

Referring now to FIGS. 25-29, in some instances, the initial position of spinal rod 321 may be such that fastener 317 is within (or immediately adjacent) intermediate threaded portion 376 of spinal rod holder 318 (see, e.g., FIGS. 27-28) upon engaging spinal rod 321. In such cases, tool 382 is first threaded through upper threaded portion 372, and end 386 of tool 382 is used to engage fastener 317 with intermediate threaded portion 376 (see FIG. 28). Tool 382 may be rotated to thereby move fastener 317 and spinal rod 321 along intermediate threaded portion 376 and lower threaded portion 380 to a fully seated position (see FIG. 29), where spinal rod 321 is proximate seating surface 315. Intermediate threaded portion 376 and lower threaded portion 380 provided an extended length of threads for spinal rod holder 318, thereby providing a greater amount of rod reduction relative to more traditional systems.

Once spinal rod 321 is properly seated and secured by fastener 317, an appropriate tool may be used to detach spinal rod guide 314 and intermediate threaded portion 376 from the remainder spinal rod holder 318. In some embodiments, a generally cylindrical, elongated tool having one or more projections is used such that the projections on the tool engage recesses 360, 362 on spinal rod guide 314 and permit a user to apply a torque to tabs 342, 344. Upon application of sufficient torque, fracture joint 365 fractures (break, etc.), enabling a user to remove the tool with spinal rod guide 314 and intermediate threaded portion 376. In various alternative embodiments, other means for removing spinal rod guide 314 and intermediate threaded portion 376 may be utilized.

In some embodiments, the tooling and spinal guide assembly disclosed herein may be configured to reduce a spinal rod a maximum of 20 mm. According to various other embodiments, the components may be configured to provide reduction of a spinal rod of greater or lesser amounts. All such applications are to be understood to be within the scope of the present disclosure.

While the invention has been illustrated and described in detail in the drawings and foregoing description, the same is to be considered as illustrative and not restrictive in character, it being understood that only exemplary embodiments have been shown and described and that all changes and modifications that come within the spirit of the invention are desired to be protected.

What is claimed is:

1. An installation kit, comprising:
    a guide assembly including an upper threaded portion and a lower threaded portion;
    a fastener; and
    a reduction tool comprising a threaded portion and an end portion configured to engage the fastener;
    wherein the end portion of the tool and the fastener are received within the guide assembly, and wherein the guide assembly and the reduction tool are configured such that upon rotation of the reduction tool relative to the guide assembly, the threaded portion of the reduction tool engages and travels longitudinally past and disengages the upper threaded portion of the guide assembly and then the fastener engages the lower threaded portion of the guide assembly; and
    wherein the upper threaded portion of the guide assembly extends fully around the reduction tool.

2. The kit of claim 1, wherein the guide assembly includes two elongated arc portions.

3. The kit of claim 2, wherein the guide assembly includes a top portion joining the two elongated arc portions, the top portion including the upper threaded portion.

4. The kit of claim 3, wherein the top portion includes an exterior surface having a plurality of flats.

5. The kit of claim 1, wherein the guide assembly includes a rod holder configured to receive a spinal rod and including the lower threaded portion.

6. The kit of claim 1, wherein the upper threaded portion has a greater thread pitch than the lower threaded portion.

7. The kit of claim 1, wherein the guide assembly includes a fracture area configured to enable a user to break off a portion of the guide assembly.

8. The kit of claim 1, wherein the upper threaded portion is spaced apart from the lower threaded portion by a non-threaded portion.

9. The installation kit of claim 1, wherein the threaded portion of the reduction tool is configured to move longitudinally along a length of the reduction tool and relative to the guide assembly to disengage the upper threaded portion of the guide assembly.

10. An installation kit, comprising:
    a guide assembly including an upper threaded portion and a lower threaded portion;
    a fastener; and
    a reduction tool comprising a threaded portion and an end portion configured to receive the fastener;
    wherein when the fastener is received on the end portion of the reduction tool, the threaded portion of the reduction tool is configured to engage the upper threaded portion of the guide assembly, and the fastener is configured to engage the lower threaded portion of the guide assembly; and
    wherein the threaded portion of the reduction tool is configured to move longitudinally along a length of the reduction tool and relative to the guide assembly to move longitudinally past and disengage the upper threaded portion of the guide assembly prior to the fastener engaging the lower threaded portion of the guide assembly.

11. The kit of claim 10, wherein the guide assembly includes two elongated arc portions.

12. The kit of claim 11, wherein the guide assembly includes a top portion joining the two elongated arc portions, the top portion including the upper threaded portion.

13. The kit of claim 12, wherein the top portion includes an exterior surface having a plurality of flats.

14. The kit of claim 10, wherein the guide assembly includes a rod holder configured to receive a spinal rod and including the lower threaded portion.

15. The kit of claim 10, wherein the upper threaded portion has a greater thread pitch than the lower threaded portion.

16. The kit of claim 10, wherein the guide assembly includes a fracture area configured to enable a user to break off a portion of the guide assembly.

17. The kit of claim 10, wherein the threaded portion of the reduction tool threadingly engages and disengages the upper threaded portion of the guide assembly before the fastener threadingly engages the lower threaded portion of the guide assembly.

18. The installation kit of claim 10, wherein the upper threaded portion of the guide assembly extends fully around the reduction tool.

19. An installation kit, comprising:
    a guide assembly including an upper threaded portion and a lower threaded portion spaced apart from the upper threaded portion by a non-threaded portion;
    a fastener; and
    a reduction tool comprising a threaded portion and an end portion configured to engage the fastener;
    wherein the end portion of the tool and the fastener are received within the guide assembly, and wherein the threaded portion of the reduction tool engages and disengages the upper threaded portion of the guide assembly and then the fastener engages the lower threaded portion of the guide assembly;
    wherein the upper threaded portion of the guide assembly extends fully around the reduction tool; and
    wherein the guide assembly and reduction tool are configured such that upon rotation of the reduction tool relative to the guide assembly, the threaded portion of the reduction tool moves longitudinally along a length of the reduction tool and relative to the guide assembly to move longitudinally past and disengage the upper threaded portion of the guide assembly prior to the fastener engaging the lower threaded portion of the guide assembly.

* * * * *